US011124489B2

(12) United States Patent
Zhou et al.

(10) Patent No.: US 11,124,489 B2
(45) Date of Patent: Sep. 21, 2021

(54) EPAC ANTAGONISTS

(71) Applicants: Jia Zhou, Galveston, TX (US); Zhiqing Liu, Galveston, TX (US); Na Ye, Galveston, TX (US); Fang Mei, Galveston, TX (US); Xiaodong Cheng, Galveston, TX (US)

(72) Inventors: Jia Zhou, Galveston, TX (US); Zhiqing Liu, Galveston, TX (US); Na Ye, Galveston, TX (US); Fang Mei, Galveston, TX (US); Xiaodong Cheng, Galveston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 16/499,050

(22) PCT Filed: Mar. 29, 2018

(86) PCT No.: PCT/US2018/025064
§ 371 (c)(1),
(2) Date: Sep. 27, 2019

(87) PCT Pub. No.: WO2018/183626
PCT Pub. Date: Oct. 4, 2018

(65) Prior Publication Data
US 2020/0255388 A1 Aug. 13, 2020

Related U.S. Application Data

(60) Provisional application No. 62/479,669, filed on Mar. 31, 2017.

(51) Int. Cl.
*C07D 261/08* (2006.01)
*C07D 261/20* (2006.01)
*A61P 31/04* (2006.01)
*A61P 31/12* (2006.01)

(52) U.S. Cl.
CPC ............ *C07D 261/08* (2013.01); *A61P 31/04* (2018.01); *C07D 261/20* (2013.01)

(58) Field of Classification Search
CPC ..... C07D 261/08; C07D 261/20; A61P 31/04; A61P 31/12
See application file for complete search history.

(56) References Cited

U.S. PATENT DOCUMENTS 3,793,456 A 2/1974 Wright et al.
2015/0110809 A1 4/2015 Cheng et al.
2016/0263088 A1 9/2016 Cheng et al.

OTHER PUBLICATIONS

Almahariq, et al., "Exchange Protein Directly Activated by cAMP Modulates Regulatory T-Cell-Mediated Immunosuppression," *Biochemical Journal*, 465(2): 295-303, 2015.
Almahariq, et al., "A Novel EPAC-Specific Inhibitor Suppresses Pancreatic Cancer Cell Migration and Invasion," *Molecular Pharmacology*, 83: 122-128, 2013.
Baljinnyam, et al., "Epac Increases Melanoma Cell Migration by A Heparan Sulfate-Related Mechanism," *American Journal of Physiology—Cell Physiology*, 297(4): 297: C802-C813, 2009.
Baljinnyam, et al., "Exchange Protein Directly Activated by Cyclic AMP Increases Melanoma Cell Migration by a Ca2+-Dependent Mechanism," *Cancer Research*, 70: 5607-5617, 2010.
Baljinnyam, et al., "Epac1 Promotes Melanoma Metastasis Via Modification of Heparan Sulfate," *Pigment Cell Melanoma Research*, 24(4): 680-687, 2011.
Baumer, et al., "Role of RAC 1 and cAMP in Endothelial Barrier Stabilization and Thrombin-Induced Barrier Breakdown," *Journal of Cellular Physiology*, 220(3): 716-726, 2009.
Berglund, et al., "Direct Leptin Action on POMC Neurons Regulates Glucose Homeostasis and Hepatic Insulin Sensitivity in Mice," *Journal of Clinical Investigation*, 122: 1000-1009, 2012.
Bryce, et al., "Immunomodulatory Effects of Pharmacological Elevation of Cyclic AMP in T Lymphocytes Proceed Via a Protein Kinase A Independent Mechanism," *Immunopharmacology*, 41: 139-146, 1999.
Chen, et al. , "Identification and Characterization of Small Molecules as Potent and Specific EPAC2 Antagonists," J Med Chem 56, 952-962, 2013.
Chen, et al., "5-Cyano-6-Oxo-1,6-Dihydro-Pyrimidines As Potent Antagonists Targeting Exchange Proteins Directly Activated by cAMP," *Bioorganic & Medicinal Chemistry Letters*, 22(12): 4038-4043, 2012.
Chen, et al., "Efficient Synthesis of ESI-09, A Novel Non-Cyclic Nucleotide EPAC Antagonist," *Tetrahedron Letters*, 54: 1546-1549, 2013.
Collison and Vignali, "In Vitro Treg Suppression Assays," *Methods in Molecular Biology*, 707: 21-37, 2011.
Cullere, et al., "Regulation of Vascular Endothelial Barrier Function by Epac, a cAMP-Activated Exchange Factor for Rap GTPase," *Blood*, 105: 1950-1955, 2005.
De Rooji, et al., "Epac is a Rap1 Guanine-Nucleotide Exchange Factor Directly Activated by Cyclic AMP," *Nature*, 396: 474-477, 1998.
Enserink, et al., "The cAMP-Epac-Rap1 Pathway Regulates Cell Spreading and Cell Adhesion to Laminin-5 Through the $\alpha_3\beta_1$ Integrin But Not the $\alpha_{6\beta4}$ Integrin," *Journal of Biological Chemistry*, 2(43)79: 44889-44896, 2004.
Fakuda, et al., "Induction of Leptin Resistance by Activation of cAMP-Epac Signaling," *Cell Metabolism*, 13: 331-339, 2011.
Fujimoto, et al., "Piccolo, a $Ca^2$ Sensor in Pancreatic β-Cells," *Journal of Biological Chemistry*, 277(52): 50497-50502, 2002.
Gloerich, et al., "The Nucleoporin RanBP2 Tethers the cAMP Effector Epac1 and Inhibits Its Catalytic Activity," Journal of Cell Biology, 193: 1009-1020, 2011.

(Continued)

*Primary Examiner* — Laura L Stockton

(57) ABSTRACT

Embodiments are directed to a series of novel EPAC antagonists that are designed, synthesized and evaluated in an effort to develop diversified analogues based on the scaffold of the previously identified high-throughput (HTS) hit ESI-09.

8 Claims, 6 Drawing Sheets

(56) References Cited

OTHER PUBLICATIONS

Gloerich, et al., "Spatial Regulation of Cyclic AMP-Epac1 Signaling in Cell Adhesion by ERM Proteins," *Molecular Cell Biology*, 30: 5421-5431, 2010.
Gong, et al., "Exchange Protein Directly Activated by cAMP Plays a Critical Role in Bacterial Invasion During Fatal Rickettsioses," *PNAS*, 110: 19615-19620, 2013.
Grandoch, et al., "The Role of Epac Proteins, Novel cAMP Mediators, In the Regulation of Immune, Lung, and Neuronal Function," *British Journal of Pharmacology*, 159, 265-284, 2010.
Howard, et al., "Enhanced Leptin Sensitivity and Attenuation of Diet-Induced Obesity in Mice with Haploinsuffienciency of Socs3," *Nature Medicine*, 10: 734-738, 2004.
International Search Report and Written Opinion Issued in Corresponding PCT Patent Application No. PCT/US2018/025064, dated Jul. 23, 2018.
Kashima, et al., "Critical Role of cAMP-GEFII Rim2 Complex in Incretin-Potentiated Insulin Secretion," *Journal of Biological Chemistry*, 276: 46046-46053, 2001.
Kawasaki, et al., "A Family of cAMP-Binding Proteins That Directly Activate Rap1," *Science*, 282: 2275-2279, 1998.
Kievit, et al., "Enhanced Leptin Sensitivity and Improved Glucose Homeostasis in Mice Lacking Suppressor of Cytokine Signaling-3 in POMC-Expressing Cells," *Cell Metabolism*, 4(2): 123-132, 2006.
Kooistra, et al., "Epac1 Regulates Integrity of Endothelial Cell Junctions Through VE-Cadherin," *FEBS Letters*, 579: 4966-4972, 2005.
Li, et al., "CD4+CD25+ Regulatory T-Cell Lines From Human Cord Blood Have Functional and Molecular Properties of T-Cell Anergy," *Blood*, 106, 3068-3073, 2005.
Li, et al., "Cyclic Adenosine 5'—Monophosphate-Stimulated Neurotensin Secretion is Mediated Through Rap1 Downstream of both Epac and Protein Kinase A Signaling Pathways," *Molecular Endocrinology*, 21: 159-171, 2007.
Liu, et al., "The Interaction of Epac1 and Ran Promotes Rap1 Activation at the Nuclear Envelope," *Molecular and Cellular Biology*, 30: 3956-3969, 2010.
Lorenz, et al., "The cAMP/EPAC1/Rap1 Pathway in Pancreatic Carcinoma," *Pancreas*, 37(1): 102-103, 2008.
Maillet, et al., "Crosstalk Between Rap1 and Rac Regulates Secretion of sAPPα," *Nature Cell Biology*, 5: 633-639, 2003.
Mei and Cheng, "Differential Signaling of Cyclic AMP Opposing Effects of Exchange Protein Directly Activated by Cyclic AMP and cAMP-Dependent Protein Kinase on Protein Kinase B Activation," *Journal of Biological Chemistry*, 277: 11497-11504, 2005.
Metrich, et al., "Role of the cAMP-Binding Protein Epac in Cardiovascular Physiology and Pathophysiology," *Pflugers Arch—European Journal of Physiology*, 459: 535-546, 2010.
Misra and Pizzo, "Epac1-Induced Cellular Proliferation in Prostate Cancer Cells is Mediated by B-Raf/ERK and mTOR Signaling Cascades," *Journal of Cellular Biochemistry*, 108: 998-1011, 2009.
Mori, et al., "Socs3 Deficiency in the Brain Elevates Leptin Sensitivity and Confers Resistance to Diet-Induced Obesity," *Nature Medicine*, 10: 739-743, 2004.
Noda, et al., "Vascular Endothelial-Cadherin Stabilizes at Cell-Cell Junctions by Anchoring to Circumferential Actin Bundles Through α- and β-Catenins in Cyclic AMP-Epac-Rap1 Signal-Activated Endothelial Cells," *Molecular Biology of the Cell*, 21: 584-596, 2010.
Ozaki, et al., "cAMP-GEFII is a Direct Target of cAMP in Regulated Exocytosis," *Nature Cell Biology*, 2: 805-811, 2000.
Qiao, et al., "Cell Cycle-Dependent Subcellular Localization of Exchange Factor Directly Activated by cAMP," *Journal of Biological Chemistry*, 277: 26581-26586, 2002.
Rampersad, et al., "Cycle AMP Phosphodiesterase 4D (PDE4D) Tethers EPAC1 in a Vascular Endothelial Cadherin (VE-Cad)-based Signaling Complex and Controls cAMP-Mediated Vascular Permeability," *Journal of Biological Chemistry*, 285: 33614-33622, 2010.
Rangarajan, et al., "Cyclic AMP Induces Integrin-Mediated Cell Adhesion Through EPAC and Rap1 Upon Stimulation of the $β_2$-adrenergic Receptor," *Journal of Cell Biology*, 160: 487-493, 2003.
Ross, et al., "Ezrin is Required for Efficient Rap1 Induced Cell Spreading," *Journal of Cell Science*, 124: 1808-1818, 2011.
Seino and Shibasaki, "PKA-Dependent and PKA-Independent Pathways for cAMP-Regulated Exocytosis," *Physiological Reviews*, 85: 1303-1342, 2005.
Shirshev, et al., "Role of Epac Proteins in Mechanisms of cAMP-Dependent Immunoregulation," *Biochemistry-Moscow*, 76(9): 981-998, 2011.
Singhmar, et al., "An Orally Active EPAC Inhibitor Reverses Mechanical Allodynia and Loss of Intraepidermal Nerve Fibers in a Mouse Model of Chemotherapy-Induced Peripheral Neuropathy," *Pain*, 159: 884-893, 2018.
Singhmar, et al., "Critical Role for EPAC1 in Inflammatory Pain Controlled by GRK2-Mediated Phosphorylation of Epac1," *PNAS*, 113: 3036-3041, 2016.
Spindler, et al., "Ultrastructural Analysis Reveals cAMP-Dependent Enhancement of Microvascular Endothelial Barrier Functions Via Rac1-Mediated Reorganization of Intercellular Junctions," *American Journal of Pathology*, 178: 2424-2436, 2011.
Staples, et al., "Evidence for Post-Transcriptional Regulation of Interleukin-5 by Dexamethasone," *Immunology*, 109: 527-535, 2003.
Tsalkova, et al., "A Fluorescence-Based High-Throughput Assay for the Discovery of Exchange Protein Directly Activated by Cyclic AMP (EPAC) Antagonists," *Plos One*, 7: e30441, 2012.
Tsalkova, et al., "Isoform-Specific Antagonists of Exchange Proteins Directly Activated by cAMP," *PNAS*, 109: 18613-18618, 2012.
Wang, et al., "Inhibition of Epac1 Suppresses Mitochondrial Fission and Reduces Neointima Formation Induced by Vascular Injury," *Scientific Reports*, 6: 36552, 2016.
Wild, et al., "Functionalized N,N-Diphenylamines as Potent and Selective EPAC2 Inhibitors," *ACS Medicinal Chemistry Letters*, 7(5): 460-464, 2016.
Ye, et al., "Structure—Activity Relationship Studies of Substituted 2-(Isoxazol-3-yl)-2-Oxo-N-Phenyl-Acetohydrazonoyl Cyanide Analogues: Identification of Potent Exchange Proteins Directly Activated by cAMP (EPAC) Antagonists," *Journal of Medicinal Chemistry*, 58: 6033-6047, 2015.
Yeager, et al., "Bacillus Anthracis Edema Toxin Suppresses Human Macrophage Phagocytosis and Cytoskeletal Remodeling Via the Protein Kinase A and Exchange Protein Activated by Cyclic AMP Pathways," *Infection and Immunity*, 77: 2530-2543, 2009.

For compounds 30 - 37: $R^2$ = 3-Cl; 3,5-di-$CF_3$; 3-Cl, 5-$CF_3$; 3-F, 5-Cl; 3-Cl, 4-F; 3-$CF_3$, 4-Cl; 3-Cl, 4-$CF_3$; 3,4,5-tri-F.

1 (cAMP)

2 (HJC0198)

3 (MAY0132)

4 ((R)-CE3F4)

5 (ESI-09)

6 (NY0123)

Reagents and conditions: (a) CH$_3$CN, CH$_3$Li, -78 °C, 1h, 64%; (b) i: 10% HCl, NaNO$_2$, H$_2$O, rt; ii: NaOAc, EtOH, rt, 84% for two steps.

Reagents and conditions: (a) 10% HCl, NaNO$_2$, H$_2$O, rt; (b) NaOAc, EtOH, rt, 84%.

EPAC ANTAGONISTS

PRIORITY PARAGRAPH

This application is a national phase under 35 U.S.C. § 371 of International Application No. PCT/US2018/025064, filed Mar. 29, 2018, which claims the benefit of priority to U.S. Provisional Patent Application Ser. No. 62/479,669, filed Mar. 31, 2017, the entire contents of each are hereby incorporated by reference in their entirety.

STATEMENT REGARDING FEDERALLY FUNDED RESEARCH

This invention was made with government support under R01GM066170, R01GM106218, R01AI111464, and R35GM122536 awarded by the National Institutes of Health. The government has certain rights in the invention.

BACKGROUND

Exchange proteins directly activated by cAMP (EPACs) were first identified as novel intracellular effector proteins of cyclic adenosine monophosphate (cAMP) by two independent groups in 1998 (de Rooij et al., *Nature* (1998) 396: 474-77; Kawasaki et al., *Science* 282 (1998) 282:2275-79). Prior to the discovery of EPAC proteins, the major physiological effects of cAMP in mammalian cells are believed to be transduced by the classic protein kinase A/cAMP-dependent protein kinase (PKA/cAPK), and cyclic nucleotide-activated ion channels (CNG and HCN) in certain tissues (Cohen, *Nat. Rev. Drug Discov.* (2002) 1:309-15; Zambon et al., *Proc. Natl. Acad. Sci. U.S.A.* (2005) 102:8561-66; Biel, *J. Biol. Chem.* (2009) 284:9017-21; Biel and Michalakis, *Handb. Exp. Pharmacol.* (2009) 111-36). Between two ubiquitously expressed intracellular cAMP receptor families, EPAC proteins, unlike PKA, have no kinase activity but act as guanine nucleotide exchange factors to catalyze the exchange of GDP with GTP for the down-stream small GTPases, Rap1 and Rap2, in response to intracellular cAMP (de Rooij et al., *Nature* (1998) 396:474-77; Kawasaki et al., *Science* 282 (1998) 282:2275-79). Two structurally homologous but functionally nonredundant isoforms of mammalian EPAC proteins have been identified, EPAC1 and EPAC2. EPAC1 is more ubiquitously expressed, whereas the expression of EPAC2 is relatively restricted, mainly found in brain, pancreatic islets and adrenal gland (Kawasaki et al., *Science* 282 (1998) 282:2275-79). From nearly two decades of research on EPAC, accumulating studies, including those with the aid of small-molecule EPAC modulators (Chen et al., *J. Med. Chem.* (2014) 57:3651-65) such as various cAMP analogues (e.g., 007-AM (Vliem et al., *Chembiochem: a European journal of chemical biology* (2008) 9:2052-54)) and newly discovered EPAC-specific antagonists (e.g., ESI-09 (Tsalkova et al., *PloS one* (2012) 7:e30441; Tsalkova et al., *Proc. Natl. Acad. Sci. U.S.A.* (2012) 109:18613-18; Almahariq et al., *Mol. Pharmacol.* (2013) 83:122-28; Gong et al., *Proc. Natl. Acad. Sci. U.S.A.* (2013) 110:19615-20; Almahariq et al., *Biochem. J.* (2015) 465:295-303)), have demonstrated that EPAC proteins play important roles in insulin secretion, energy homeostasis, cardiovascular response, pain sensing, osteoclast differentiation, neurotransmitter release, Treg-mediated immune suppression, integrin-mediated cell adhesion, cell migration and proliferation, cell exocytosis, and apoptosis as well as gene transcription and chromosomal integrity (Grandoch et al., *Br. J. Pharmacol.* (2010) 159:265-84; Breckler et al., *Cell. Signalling* (2011) 23:1257-66; Gloerich and Bos, *Annu. Rev. Pharmacol. Toxicol.* (2010) 50:355-75; Almahariq et al., *Mol. Pharmacol.* (2015) 87:142-49; Schmidt et al., *Pharmacol. Rev.* (2013) 65:670-709; Robichaux and Cheng, *Physiol. Rev.* (2018) 98:919-1053), and thus represent potential therapeutic targets for various human diseases such as cancer, bacterial and viral infections, chronic pain, diabetes, obesity, and heart failure.

Our previous high-throughput screening (HTS) campaign using automated, robust, and sensitive fluorescence based competition assay (Tsalkova et al., *PloS one* (2012) 7:e30441; Tsalkova et al., *Proc. Natl. Acad. Sci. U.S.A.* (2012) 109:18613-18) led to the identification of several EPAC specific inhibitors (ESIs), and was subsequently followed by extensive hit-to-lead optimizations (Chen et al., *Tetrahedron Lett.* (2013) 54:1546-49; Chen et al., *J. Med. Chem.* (2013) 56:952-62; Chen et al., *Bioorg. Med. Chem. Lett.* (2012) 22:4038-43; Wild et al., *ACS Med. Chem. Lett.* (2016) 7:460-64; Ye et al., *J. Med. Chem.* (2015) 58:6033-47). Among these identified inhibitor hits, ESI-09 (1, FIG. 1) has been shown to selectively inhibit EPAC functions in vitro (Almahariq et al., *Mol. Pharmacol.* (2013) 83:122-28) and in vivo (Gong et al., *Proc. Natl. Acad. Sci. U.S.A.* (2013) 110:19615-20; Almahariq et al., *Mol. Pharmacol.* (2015) 87:142-49; Almahariq et al., *Biochem. J.* (2015) 465:295-303; Wang et al., *Sci. Rep.* (2016) 6:36552; Singhmar et al., *PNAS* (2016) 113:3036-3041; Singhmar et al., *Pain* (2018) 159). With the aid of molecular docking studies of 1 into the cAMP binding domain B of active EPAC2 proteins, it is hypothesized that binding interactions of inhibitors to EPAC2 proteins may primarily occur through two terminal hydrophobic pockets (P1 and P2) and the unique linker. Later, systematic structure-activity relationships (SARs) studies were performed, leading to the discovery of several more active EPAC antagonists with low micromolar inhibitory activity and improved solubility (Ye et al., *J. Med. Chem.* (2015) 58:6033-47).

There remains a need for additional EPAC agonists having a variety of characteristics.

SUMMARY

In a continuing effort to develop novel diversified analogs based on the scaffold of hit 1, the inventors focused on further chemical optimizations involving modifications of 5-tert-butyl group on the isoxazole ring A, meanwhile retaining favorable hydrophobic fragments of EPAC antagonists including fluorine-substitutions on the B-ring identified from previous studies (Ye et al., *J. Med. Chem.* (2015) 58:6033-47). In order to explore the depth of the aforementioned hydrophobic pocket P2, as depicted in FIG. 1, series I was designed by inserting a rigid phenyl ring between the isoxazole A ring and its tert-butyl substitution at the 5-position. For comparison, an attempt was made to keep the molecular skeleton more compacted by fusing a phenyl ring with the isoxazole A (as depicted in series II, FIG. 1).

Herein, such structural modifications of compound 1 are described with a focus on improved EPAC inhibitory activities and structural diversity of EPAC antagonists. The studies have resulted in the discovery of several novel potent EPAC antagonists such as 14 (NY0460), 26 (NY0725), 32 (NY0561), and 33 (NY0562), with low micromolar inhibitory activities for preclinical development, as well as others.

A series of novel EPAC antagonists have been designed, synthesized, and evaluated in an effort to develop diversified analogues based on the scaffold of the previously identified high-throughput (HTS) hit ESI-09 (1).

Certain embodiments are directed to an Exchange Protein Activated by cAMP (EPAC) antagonist having a formula of:

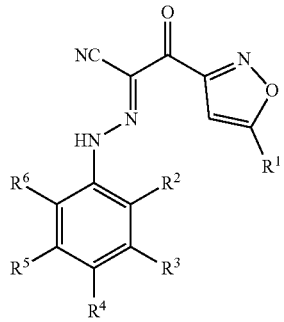

Formula I where $R^1$ is phenyl, substituted phenyl, or furanyl; $R^2$ and $R^6$ are H; $R^3$, $R^4$, and $R^5$ are independently selected from H, halogen, $CF_3$, C1 to C4 alkyl, C1 to C4 heteroalkyl, C1 to C4 alkoxy; and specifically excluding a compound where $R^1$ is phenyl, and $R^3$, $R^4$ and $R^5$ are chloro. In certain aspects $R^1$ is a substituted phenyl. In a further aspect the substituted phenyl is a substituted at the 4 position. The $R^1$ position can be a phenyl, 4-(tert-butyl)-phenyl, 4-fluoro-phenyl, 4-chloro-phenyl, 4-methoxy-phenyl, or furanyl-2-yl. In certain aspects $R^3$, $R^4$, $R^5$ are independently selected from H, chloro, fluoro, or trifluoromethyl. In a particular aspect the compound is N-(4-Chloro-3-(trifluoromethyl)phenyl)-2-oxo-2-(5-(4-(tert-butyl)phenyl)isoxazol-3-yl)acetohydrazonoyl cyanide (NY0617), N-(3-trifluromethyl-4-chlorophenyl)-2-oxo-2-(5-phenylisoxazol-3-yl)acetohydrazonoyl cyanide (NY0460), N-(3,5-Bis(trifluoromethyl)phenyl)-2-oxo-2-(5-phenylisoxazol-3-yl)acetohydrazonoyl cyanide (NY0457), N-(4-Chloro-3-(trifluoromethyl)phenyl)-2-oxo-2-(5-(4-methoxyphenyl)isoxazol-3-yl)acetohydrazonoyl cyanide (NY0654), N-(3,5-bis(trifluoromethyl)phenyl)-2-(5-(4-chlorophenyl)isoxazol-3-yl)-2-oxoacetohydrazonoyl cyanide (NY0655), N-(3-Chloro-5-(trifluoromethyl)phenyl)-2-(5-(furan-2-yl)isoxazol-3-yl)-2-oxoacetohydrazonoyl cyanide (NY0725), or N-(4-Chloro-3-(trifluoromethyl)phenyl)-2-(5-(furan-2-yl)isoxazol-3-yl)-2-oxoacetohydrazonoyl cyanide (NY0726).

Certain embodiments are directed to an Exchange Protein Activated by cAMP (EPAC) antagonist having a formula of:

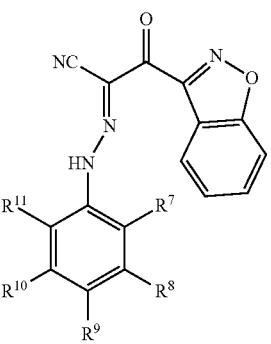

Formula II where $R^7$ and $R^{11}$ are H; $R^8$, $R^9$, and $R^{10}$ are independently selected from H, halogen, $CF_3$, C1 to C4 alkyl, C1 to C4 heteroalkyl, C1 to C4 alkoxy. In certain aspects $R^8$, $R^9$, and $R^{10}$ are independently selected from H, chloro, fluoro, or trifluoromethyl. In a particular aspect the compound is selected from 2-(benzo[d]isoxazol-3-yl)-N-(3-chloro-5-(trifluoromethyl)phenyl)-2-oxoacetohydrazonoyl cyanide (NY0495), 2-(benzo[d]isoxazol-3-yl)-N-(3-chloro-4-(trifluoromethyl)phenyl)-2-oxoacetohydrazonoyl cyanide (NY0561), or 2-(benzo[d]isoxazol-3-yl)-N-(4-chloro-3-(trifluoromethyl)phenyl)-2-oxoacetohydrazonoyl cyanide (NY0562).

Certain embodiments are directed to an Exchange Protein Activated by cAMP (EPAC) antagonist having a formula of:

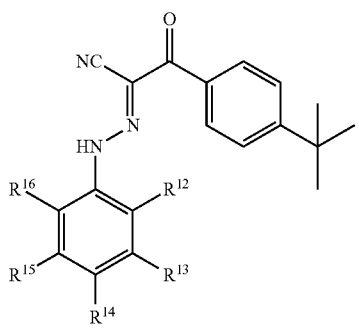

Formula III where $R^{12}$ and $R^{16}$ are H; $R^{13}$, $R^{14}$, and $R^{15}$ are independently selected from H, halogen, $CF_3$, C1 to C4 alkyl, C1 to C4 heteroalkyl, C1 to C4 alkoxy; and specifically excluding a compound where (i) $R^{15}$ is H, and $R^{13}$ and $R^{14}$ are chloro, and (ii) $R^{13}$ and $R^{15}$ are H, and $R^{14}$ is chloro. In certain aspects $R^{13}$, $R^{14}$, and $R^{15}$ are independently selected from H, chloro, fluoro, or trifluoromethyl. In particular aspects the compound is (E)-2-(4-(tert-butyl)phenyl)-N-(3-chlorophenyl)-2-oxoacetohydrazonoyl cyanide (ZL0474); (E)-2-(4-(tert-butyl)phenyl)-N-(3,5-dichlorophenyl)-2-oxoacetohydrazonoyl cyanide (ZL0475); (E)-2-(4-(tert-butyl)phenyl)-N-(3-chloro-4-fluorophenyl)-2-oxoacetohydrazonoyl cyanide (ZL0476); (E)-2-(4-(tert-butyl)phenyl)-N-(3-chloro-5-fluorophenyl)-2-oxoacetohydrazonoyl cyanide (ZL0477); (E)-2-(4-(tert-butyl)phenyl)-2-oxo-N-(3,4,5-trifluorophenyl)acetohydrazonoyl cyanide (ZL0478); (E)-N-(3,5-bis(trifluoromethyl)phenyl)-2-(4-(tert-butyl)phenyl)-2-oxoacetohydrazonoyl cyanide (ZL0479); (E)-2-(4-(tert-butyl)phenyl)-N-(4-chloro-3-(trifluoromethyl)phenyl)-2-oxoacetohydrazonoyl cyanide (ZL0559); (E)-2-(4-(tert-butyl)phenyl)-N-(3-chloro-5-(trifluoromethyl)phenyl)-2-oxoacetohydrazonoyl cyanide (ZL0560); (E)-2-(4-(tert-butyl)phenyl)-N-(3-chloro-4-(trifluoromethyl)phenyl)-2-oxoacetohydrazonoyl cyanide (ZL0561); or (E)-2-(4-(tert-butyl)phenyl)-2-oxo-N-(3,4,5-trichlorophenyl)acetohydrazonoyl cyanide (ZL0562).

Certain embodiments are directed to an Exchange Protein Activated by cAMP (EPAC) antagonist having a formula of:

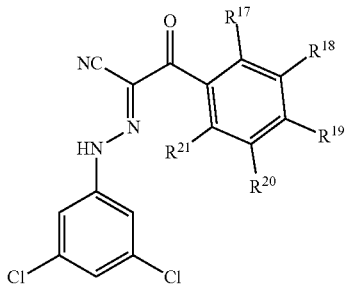

Formula IV where $R^{17}$ and $R^{21}$ are H; $R^{18}$, $R^{19}$, and $R^{20}$ are independently selected from H, halogen, $CF_3O$, $CF_3$, C1 to C4 alkyl, C1 to C4 heteroalkyl, C1 to C4 alkoxy, C1 to C4 heteroalkoxy, C1 to C4 ester, or phenyl; and specifically excluding a compound where $R^{18}$, $R^{19}$, and $R^{20}$ are H. In certain aspects $R^{18}$, $R^{19}$, and $R^{20}$ are independently selected from H, chloro, fluoro, methyl ester, trifluoromethyl, substituted or unsubstituted cycloalkyl, or substituted or unsubstituted heterocycle. In particular aspects the compound is (E)-2-(4-chlorophenyl)-N-(3,5-dichlorophenyl)-2-oxoacetohydrazonoyl cyanide (ZL0491); (E)-2-(3-chlorophenyl)-N-(3,5-dichlorophenyl)-2-oxoacetohydrazonoyl cyanide (ZL0546); (E)-N-(3,5-dichlorophenyl)-2-oxo-2-(4-(trifluoromethoxy)phenyl)acetohydrazonoyl cyanide (ZL0564); Methyl (E)-4-(2-cyano-2-(2-(3,5-dichlorophenyl)hydrazono)acetyl)benzoate (ZL0566); (E)-2-([1,1'-biphenyl]-4-yl)-N-(3,5-dichlorophenyl)-2-oxoacetohydrazonoyl cyanide (ZL0536); (E)-N-(3,5-dichlorophenyl)-2-(3,4-dimethoxyphenyl)-2-oxoacetohydrazonoyl cyanide (ZL0631); (E)-N-(3,5-dichlorophenyl)-2-oxo-2-(4-(piperidin-1-ylmethyl)phenyl)acetohydrazonoyl cyanide (ZL0644); (E)-N-(3,5-dichlorophenyl)-2-(4-(morpholinomethyl)phenyl)-2-oxoacetohydrazonoyl cyanide (ZL0668); or (E)-2-(4-cyclohexylphenyl)-N-(3,5-dichlorophenyl)-2-oxoacetohydrazonoyl cyanide (ZL0634).

Certain aspects are directed to an Exchange Protein Activated by cAMP (EPAC) antagonist having a formula of:

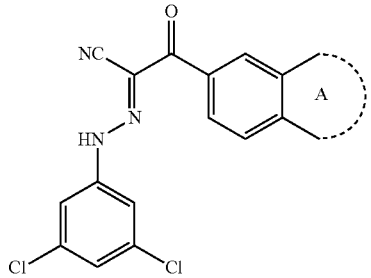

Formula V where A is a cycloalkyl, heterocyclyl, aryl, or heteroaryl. In particular aspects the compound is (E)-N-(3,5-dichlorophenyl)-2-oxo-2-(5,6,7,8-tetrahydronaphthalen-2-yl)acetohydrazonoyl cyanide (ZL0524); (E)-N-(3,5-dichlorophenyl)-2-(naphthalen-2-yl)-2-oxoacetohydrazonoyl cyanide (ZL0682); or (E)-N-(3,5-dichlorophenyl)-2-oxo-2-(quinolin-6-yl)acetohydrazonoyl cyanide (ZL0642).

Embodiments can be directed to pharmaceutically acceptable salt of the compounds described herein.

In certain aspects the invention is directed to methods for selectively modulating EPAC comprising contacting EPAC with a compound described herein. In certain aspects modulating EPAC is negatively modulating or antagonizing EPAC. In certain embodiments EPAC can be antagonized to treat diabetes, chronic pain, neuropathic pain, peripheral neuropathy, chemotherapy induced peripheral neuropathy, heart failure, cancer, atherosclerosis, pathologic inflammation, or neointima formation.

In a further aspect methods are directed to treating cancer comprising administering an EPAC specific inhibitor to a subject having cancer, wherein the EPAC specific inhibitor is a compound described herein.

Still a further aspect is directed to methods of enhancing an immune response comprising administering an EPAC specific inhibitor to a subject, wherein the EPAC specific inhibitor is a compound described herein. In certain aspects the method can further include administering an antigen or a therapeutic antibody.

Certain aspects are directed to methods of enhancing leptin sensitivity comprising administering an EPAC specific inhibitor to a subject having leptin resistance, wherein the EPAC specific inhibitor is a compound described herein.

A further aspect is directed to methods of suppressing microbe infection comprising administering an EPAC specific inhibitor to a subject having or under the risk of microbe infection, wherein the EPAC specific inhibitor is a compound described herein. In certain aspects the microbe is a bacteria, virus, or fungi.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(FIG. 1A) Drug design strategy for the current work. (FIG. 1B) Scheme 1. Synthesis of the 2-oxo-N-phenyl-2-(5-phenylisoxazol-3-yl)acetohydrazonoyl cyanide analogues 7-27. Reagents and conditions: (a) $CH_3CN$, MeLi, THF, −78° C.; or $CH_3CN$, NaH, THF, 50° C.; (b) 2 N HCl, $NaNO_2$, $H_2O$, 0° C.; (c) 4a-f, NaOAc, EtOH, 14-81% for three steps. (FIG. 1C) Scheme 2. Synthesis of 2-(benzo[d]isoxazol-3-yl)-2-oxo-N-phenylacetohydrazonoyl Cyanide Analogues 30-37. Reagents and conditions: (a) $CH_3CN$, MeLi, THF, −78° C.; (b) 6a-h, NaOAc, EtOH, 22-57% for two steps.

(FIG. 6A) Design strategy of 2-substituted phenyl-N-phenyl-2-oxoacetohydrazonoyl cyanides using a bioisosteric replacement approach. (FIG. 6B) Scheme 1. Synthesis of compounds 11~20. (FIG. 6C) Scheme 2. Synthesis of compounds 24~34.

DESCRIPTION

Figure 1A:
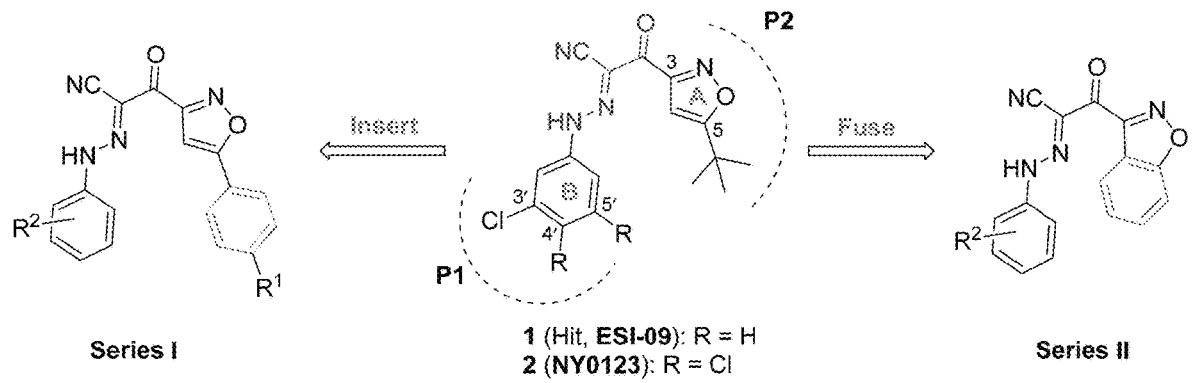
FIGS. 1A-1C.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of that embodiment, and not intended to intimate that the scope of the disclosure, including the claims, is limited to that embodiment.

I. Methods of Using EPAC Modulators

Cyclic adenosine monophosphate (cAMP) is an important component of cell-signaling networks that control numerous biological processes. More than a decade of extensive studies have now firmly established that many cAMP-related cellular processes, previously thought to be controlled by PKA alone, are also mediated by EPAC (Gloerich and Bos, (2010) *Annu Rev Pharmacol Toxicol* 50:355-375). For example, EPAC proteins have been implicated in regulating exocytosis and secretion (Ozaki et al. (2000) *Nat Cell Biol* 2:805-811; Seino and Shibasaki (2005) *Physiol Rev* 85:1303-1342; Maillet et al. (2003) *Nat Cell Biol* 5:633-639; Li et al. (2007) *Mol Endocrinol* 21:159-171), cell adhesion (Enserink et al. (2004) *J Biol Chem* 279:44889-44896; Rangarajan et al. (2003) *J Cell Biol* 160:487-493), endothelial barrier junctions (Cullere et al. (2005) *Blood* 105:1950-1955; Kooistra et al. (2005) *FEBS Lett* 579:4966-4972), leptin signaling, and cardiac functions (Metrich et al. (2010) *Pflugers Arch* 459:535-546). In addition to its regulatory functions under physiological conditions, cAMP has been implicated in playing a major role in multiple human diseases, including cancer, diabetes, heart failure, and neurological disorders, such as Alzheimer's disease (AD). The EPAC1 and/or EPAC2 modulating compounds described herein can be used to provide treatment for a variety of diseases or conditions associated with EPAC activation or inhibition. In certain aspect EPAC inhibition is used to treat diabetes, chronic pain, neuropathic pain, peripheral neuropathy, chemotherapy induced peripheral neuropathy, heart failure, cancer, atherosclerosis, pathologic inflammation, or neointima formation.

A. Treating Chronic or Neuropathic Pain

Embodiments are directed to methods and/or a medicament for the prevention and/or treatment of chronic or neuropathic pain and/or symptoms of chronic or neuropathic pain in an individual. In certain aspects, the methods are directed to providing or administering an EPAC inhibitor for the prevention and/or treatment of chronic pain and/or symptoms of chronic pain. In certain aspects the EPAC inhibitor is prepared for administration to a subject experiencing chronic or neuropathic pain. A further aspect is directed to the use of an EPAC inhibitor for the manufacture of a medicament for ameliorating, controlling, reducing incidence of, or delaying the development or progression of chronic pain and/or symptoms of chronic pain. Certain aspects are directed to methods of preventing and/or treating chronic pain and/or symptoms of chronic pain in an individual, comprising administering to the individual of an effective amount of an EPAC inhibitor. In certain aspects the individual or subject is a mammal, for example a companion animal such as a horse, cat or dog or a farm animal such as a sheep, cow or pig. In a further aspect the mammal is a human.

In certain embodiments the medicament and/or EPAC inhibitor is prepared for oral, sublingual, buccal, topical, rectal, inhalation, transdermal, subcutaneous, intravenous, intra-arterial, intrathecal, intramuscular, intraosseous, intradermal, intraperitoneal, transmucosal, intra-articular, peri-articular, local, epidural, or epicutaneous administration.

According to certain embodiments the medicament is prepared for administration prior to and/or during and/or after the development of chronic pain or administration of a therapy (e.g., chemotherapy, surgery, etc.). In certain aspects the EPAC inhibitor is administered centrally, spinally, or intrathecally.

In certain aspects the chronic pain is chronic nociceptive pain, chronic neuropathic pain, chronic inflammatory pain, chemotherapy-induced pain, fibromyalgia, breakthrough pain and/or persistent pain. The chronic pain may comprise one or more of hyperalgesia, allodynia, central sensitization, peripheral sensitization, disinhibition, and spontaneous pain.

In certain aspects the chronic pain is cancer pain, preferably cancer pain arising from malignancy or from cancer. The cancer can be one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukemia, primary or secondary bone cancer, tumors that metastasize to the bone, tumors infiltrating the nerve and hollow viscus, tumors near neural structures. Further preferably the cancer pain comprises visceral pain, such as visceral pain that arises from pancreatic cancer and/or metastases in the abdomen. Further preferably the cancer pain comprises somatic pain, preferably somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

In certain aspects the cancer associated neuropathic pain is chemotherapy-induced neuropathic pain associated with chemotherapy-induced peripheral neuropathy (CIPN). CIPN is a frequent, dose-dependent complication of anticancer drugs including platinums, taxanes, epothilones, and vinca alkaloids. CIPN presents clinically as deficits in sensory, motor, and sometimes autonomic function. Sensory disturbances range from a mild tingling sensation to spontaneous burning pain and hypersensitivity to stimuli. Symptoms may occur at any time during the course of chemotherapy or even after termination.

In a further aspect the EPAC inhibitor is administered separately, sequentially or simultaneously (co-administered or co-formulated) in combination with one or more further pharmacologically active compounds or agents (i.e., secondary agents). In certain aspects, secondary agent can include agents useful for treating chronic pain. In one aspect the additional agent(s) is/are selected from one or more of:

(i) an opioid analgesic, e.g. morphine, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(ii) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398, or a pharmaceutically acceptable salt thereof;

(iii) a barbiturate sedative, e.g. amobarbital, aprobarbital, butabarbital, butabital, mephobarbital, metharbital, methohexital, pentobarbital, phenobartital, secobarbital, talbutal, theamylal or thiopental or a pharmaceutically acceptable salt thereof;

(iv) a sedative, e.g. glutethimide, meprobamate, methaqualone, dichloralphenazone chlordiazepoxide, clorazepate, diazepam, flurazepam, lorazepam, oxazepam, temazepam, triazolam, diphenhydramine, pyrilamine, promethazine, chlorpheniramine, chlorcyclizine or a pharmaceutically acceptable salt thereof;

(v) a skeletal muscle relaxant, e.g. baclofen, carisoprodol, chlorzoxazone, cyclobenzaprine, methocarbamol or orphrenadine or a pharmaceutically acceptable salt thereof; or (vi) other drugs such as dextromethorphan ((+)-3-hydroxy-N-methylmorphinan), dextrorphan ((+)-3-hydroxy-N-methylmorphinan), ketamine, memantine, pyrroloquinoline quinone, cis-4-(phosphonomethyl)-2-piperidinecarboxylic acid, doxazosin, tamsulosin, clonidine, 4-amino-6,7-dimethoxy-2-(5-methanesulfonamido-1,2,3,4-tetrahydroisoquinol-2-yl)-5-(2- pyridyl) quinazoline, carbamazepine, valproate, (αR, 9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant, 3-[[2-methoxy-5-(trifluoromethoxy)phenyl]methylamino]-2-phenyl-piperidine (2S,3S), oxybutin, tolterodine, propiverine, tropsium chloride, darifenacin, paracetamol, droperidol, resiniferatoxin, capsazepine, propranolol, mexiletine, dexamethasone, sildenafil, vardenafil, taladafil, gabapentin, pregabalin, desipramine, imipramine, amytriptiline, nortriptiline, amitriptyline (Elavil), trazodone (Desyrel), imipramine (Tofranil), phenyloin (Dilantin) or carbamazepine (Tegretol).

In further embodiments the secondary agent can be a therapeutic agent, such as an anti-cancer agent (e.g., a chemotherapeutic) or anti-diabetic agent.

Certain aspects are directed to providing a pharmaceutical composition for the prevention and/or treatment of chronic pain and/or symptoms of chronic pain or for ameliorating, controlling, reducing incidence of, or delaying the development or progression of chronic pain and/or symptoms of chronic pain in an individual, comprising an EPAC inhibitor and a pharmaceutically acceptable carrier and/or an excipient.

In one embodiment, "prepared for" herein means the medicament is in the form of a dosage unit or the like suitably packaged and/or marked for use in treating chronic pain.

"Reducing incidence" of chronic pain and/or a symptom associated with chronic pain means any of reducing severity (which can include reducing need for and/or amount of (e.g., exposure to) other drugs and/or therapies generally used for these conditions), duration, and/or frequency.

"Ameliorating" chronic pain and/or a symptom associated with chronic pain means a lessening or improvement of one or more symptoms of chronic pain and/or symptoms associated with chronic pain as compared to not administering an EPAC inhibitor. "Ameliorating" also includes shortening or reduction in duration of a symptom.

"Palliating" chronic pain and/or a symptom associated with chronic pain means lessening the extent of one or more undesirable clinical manifestations of chronic pain in an individual or population of individuals treated with an EPAC inhibitor in accordance with the invention.

As used therein, "delaying" the development of chronic pain means to defer, hinder, slow, retard, stabilize, and/or postpone progression of chronic pain and/or a symptom associated with chronic pain. This delay can be of varying lengths of time, depending on the history of the disease and/or individuals being treated. As is evident to one skilled in the art, a sufficient or significant delay can, in effect, encompass prevention, in that the individual does not develop chronic pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

B. Cardiovascular Indications

EPAC has a demonstrated role in the regulation of various cAMP-dependent cardiovascular functions, such as calcium handling and vascular tone. EPAC proteins are coupled to a multitude of effectors into distinct subcellular compartments because of their multidomain architecture. These novel cAMP sensors are not only at the crossroads of different physiological processes but also may represent attractive therapeutic targets for the treatment of several cardiovascular disorders, including atherosclerosis, restenosis, cardiac arrhythmia and heart failure. Certain aspects are directed to treating cardiovascular indications or cardiovascular disease in a subject by administering an EPAC inhibitor. As used herein, the term "cardiovascular indication" encompasses all types of cardiovascular conditions that, regardless of their cause, are generally recognized by a physician as heart failure, which include but are not limited to, acute heart failure, chronic heart failure, congestive heart failure (CHF), and particularly acute decompensated heart failure (which is a separate and distinct disease state than CHF). In this application, the terms acute decompensated heart failure ("ADHF") and decompensated heart failure ("DHF") are used interchangeably. These conditions typically involve weakened heart function combined with a build-up of body fluid and may be the result of either a sudden event, such as myocardial infarction or the rupture of a heart valve, or a chronic and slowly progressing process, such as the gradual weakening of heart muscles due to cardiomyopathy from infections or alcohol/drug abuse, and other pre-existing medical conditions such as hypertension, coronary artery disease, valve disease, thyroid disease, kidney disease, diabetes, or congenital heart defects. Also encompassed by the term "heart failure" are any heart conditions relating to fluid build-up in the heart, such as myocardial edema.

EPAC inhibitors can be combined with one or more additional therapies for cardiovascular or related disorders, e.g., insulin therapy, vascular surgery, cardiac surgery, angioplasty, or treatment with andrenergic blockers, coronary vasodilators, calcium channel blockers, nitrates, angiotensin converting enzyme inhibitors, anti-hypertensives, anti-inflammatory agents, diuretics, anti-arrhythmia agents, thrombolytic agents, enzyme inhibitors such as hydroxymethylglutaryl CoA reductase inhibitors or xanthine oxidase inhibitors. Examples of hydroxymethylglutaryl CoA reductase inhibitors include statins such as mevastatin, lovastatin, pravastatin, simvastatin or similar compounds. Other therapies that can be applied include diet control, dietary calorie restriction or diet modification for subjects who are or who are susceptible to developing a cardiovascular or related condition such as pulmonary hypertension, diabetes, a dyslipidemia or obesity, e.g., humans having a body mass index of 27, 28, 29, 30, 31, 32, 33, 34, 35, 36 or greater. Diet modifications include limiting or restricting salt, alcohol, caffeine, cigarette, drugs (e.g., opiate, hallucinogen, sedative, narcotic or amphetamine), sugar, refined sugar and/or fat or cholesterol intake, use or abuse. Additional therapies include treatment with one or more of digoxin, nitroglycerin, doxazosin mesylate, nifedipine, enalapril maleate, indomethicin, tissue plasminogin activator, urokinase, acetylsalicylic acid or the like. Any of such additional therapies would be used essentially according to standard protocols and such therapies would precede, be concurrent with or follow treatment with an EPAC inhibitor. In some embodiments, such additional therapies will be administered at the same time that an EPAC inhibitor is being used or within about 1 day to about 16 weeks before or after at least one round of treatment with the EPAC inhibitor is completed. Other exemplary therapeutic agents and their use have been described in detail, see, e.g., Physicians Desk Reference 54th edition, 2000, pages 303-3251, ISBN 1-56363-330-2, Medical Economics Co., Inc., Montvale, N.J.; Harrison's Principles of Internal Medicine, 15th edition, 2001, E. Braunwald, et al., editors, McGraw-Hill, New York, N.Y., ISBN 0-07-007272-8, especially chapters 231, 241-248 and 258-265 at pages 1309-1318, 1377-1442 and 1491-1526. One or more of these agents or treatments can be used in combination with an EPAC inhibitor to treat any of the appropriate cardiovascular and related disorders described herein.

C. Cancer Therapy

Certain aspects are directed to treating cancer or cancer metastasis in a subject by administering an EPAC inhibitor.

Like PKA, EPAC contains an evolutionarily conserved cAMP-binding domain that acts as a molecular switch for sensing intracellular levels of the second messenger cAMP, and activates the down-stream signaling molecules small GTPases Rap1 and Rap2 (de Rooij et al. (1998) *Nature* 396:474-477; Kawasaki et al. (1998) *Science* 282:2275-2279). In addition, EPAC proteins exert their functions through interactions with other cellular partners at specific cellular locations. For example, EPAC1 is known to associated with mitotic spindle, plasma membrane and nuclear membrane by interacting with tubulin (Qiao et al. (2002) *J Biol Chem* 277:26581-26586; Mei and Cheng (2005) *J Biol Chem* 277:11497-11504), ezrin-radixin-moesin (ERM) proteins (Gloerich et al. (2010) *Mol Cell Biol* 30:5421-5431; Ross et al. (2011) *J Cell Sci* 124:1808-1818) and nucleoporin RanBP2 (Liu et al. (2010) *Mol Cell Biol* 30:3956-3969; Gloerich et al. (2011) *J Cell Biol* 193:1009-1020), respectively. On the other hand, EPAC2 can interact with Rim (Rab3 interacting molecule) and Rim2 (Kashima et al. (2001) *J Biol Chem* 276:46046-46053; Ozaki et al. (2000) *Nat Cell Biol* 2:805-811), as well as a structurally related calcium sensor Piccolo (Fujimoto et al. (2002) *J Biol Chem* 277:50497-50502). In pancreatic beta cells, interactions among EPAC2, Rim2 and Piccolo are critical for cAMP-mediated insulin secretion (Ozaki et al. (2000) *Nat Cell Biol* 2:805-811; Kashima et al. (2001) *J Biol Chem* 276:46046-46053; Fujimoto et al. (2002) *J Biol Chem* 277:50497-50502).

Pancreatic ductal adenocarcinoma (PDAC) is one of the most lethal human diseases, largely due to the fact that pancreatic cancer is resistant to treatments that are usually effective for other types of cancer. A better understanding of the molecular mechanism of PDAC development and metastasis and effective therapeutics are desperately needed. Recently, it has been shown that EPAC1 is markedly elevated in human PDAC cells as compared with normal pancreas or surrounding tissue (Lorenz et al. (2008) *Pancreas* 37:102-103). EPAC1 has been implicated in promoting cellular proliferation in prostate cancer (Misra and Pizzo (2009) *J Cell Biochem* 108:998-1011; Misra and Pizzo (2011) *J Cell Biochem* 112(6):1685-95) and migration and metastasis in melanoma (Baljinnyam et al. (2011) *Pigment Cell Melanoma Res* 24:680-687; Baljinnyam et al. (2009) *Am J Physiol Cell Physiol* 297:C802-C813; Baljinnyam et al. (2010) *Cancer Res* 70:5607-5617).

EPAC inhibitor ESI-09 is used to demonstrate a functional role for EPAC1 overexpression in pancreatic cancer cell migration and invasion. These findings are consistent with similar results based on RNAi silencing techniques, suggesting that EPAC 1 is a target for therapeutic strategies in PDAC and other cancers.

In certain embodiments an EPAC inhibitor can be administered for the treatment of cancer. In certain aspects the cancer is pancreatic cancer, prostate cancer, melanoma, bladder cancer, blood cancer, bone cancer, brain cancer, breast cancer, colorectal cancer, esophageal cancer, gastrointestinal cancer, liver cancer, lung cancer, nasopharynx cancer, ovarian cancer, stomach cancer, testicular cancer, or uterine cancer. In still a further aspect the cancer is pancreatic cancer, particularly pancreatic ductal adenocarcinoma (PDAC). In certain aspects the EPAC inhibitor is selected from the EPAC inhibitors described herein. In a further aspect the EPAC inhibitor is an EPAC 1 inhibitor.

D. Immune Modulator

Certain methods are directed to modulating the innate or adaptive immune system of a subject by administering an EPAC modulator. In a further aspect, methods include enhancing an immune response in a subject by administering an EPAC inhibitor. The immune response can be directed to microbes (fungi, virus, bacteria, and the like); abnormal or aberrantly functioning cells, such as cancer cells or hypersensitive immune effectors; or other pathological conditions that would benefit from an enhanced immune response. Immune modulation is a critical aspect for the treatment of a number of diseases and disorders. T cells in particular play a vital role in fighting infections and have the capability to recognize and destroy cancer cells. Enhancing T cell mediated responses is a key component to enhancing responses to a number of therapeutic agents.

Cyclic AMP is a potent negative regulator of T-cell mediated immunity as it inhibits T-cell proliferation, activation, cytotoxic function, and production of Th1 pro-inflammatory cytokines (Mosenden and Taskén (2011) *Cell Signal* 23, 1009-16; Vang et al. (2001) *J Exp Med* 193, 497-507; Skalhegg et al. (1992) *J Biol Chem* 267, 15707-14; Henney et al. (1972) *J Immunol* 108, 1526-34; Kammer (1988) *Immunol Today* 9, 222-9; Hermann-Kleiter et al. (2006) *Blood* 107, 4841-8). EPAC1 and EPAC2 mediates several of the cAMP immunoregulatory effects that were originally ascribed to protein kinase A (Shirshev (2011) *Biochemistry (Mosc)* 76, 981-98; Bryce et al. (1999) *Immunopharmacology* 41, 139-46; Staples et al, (2003) *Immunology* 109, 527-35; Grandoch et al. (2010) *Br J Pharmacol* 159, 265-84). The EPAC1 effector Rap1 is activated in human CD4+CD25+ upon stimulation (Li et al. (2005) *Blood* 106, 3068-73), suggesting EPAC1 exerts broad control over the immune response in addition to regulating specific effector functions of T-cell mediated immunity.

Several findings support this notion. Transgenic mice expressing a constitutively active Rap1 had lower levels of pro-inflammatory cytokines and an increased fraction of the CD4+CD103+ Tregs subset (including CD4+CD103+ CD25+), which suppressed CD4+CD25– (Tconv) cells more potently than their WT counterparts (Li et al. (2005) *J Immunol* 175, 3133-9). More recently, it was shown that Tregs suppress effector T-cells by direct transfer of cAMP through gap junctions (Fassbender et al. (2010) *Cell Immunol* 265, 91-6; Vignali et al. (2008) *Nat Rev Immunol* 8, 523-32; Somekawa et al. (2005) *Circ Res* 97, 655-62), whose formation in cardiac cells is enhanced by EPAC1 as it facilitates the accumulation of connexons at the site of gap junction formation (Collison and Vignali (2011) *Methods Mol Biol* 707, 21-37). These findings suggest that EPAC1 might play a direct role in contact dependent Treg suppression. To study the in vivo functions of EPAC1, the inventors generated Epac1 knockout (KO) mice. Epac1$^{-/-}$ mice were orally immunized with ovalbumin (OVA) alone or with cholera toxin (CT). In each case Epac1 KO mice had a significantly higher level of serum OVA-specific IgG1 antibodies than that of wild-type (WT) mice as determined by ELISA. Furthermore, when WT mice were orally immunized with OVA alone or with an EPAC specific antagonist (ESI-09) the mice receiving ESI-09 (oral gavage 50 mg/kg) had a significantly higher level of serum OVA-specific IgG1 antibodies than that of the control group treated with vehicle.

Based on the amplified immune response in Epac1 KO mice, both antigen-challenged and naïve, it was suggested that a role for Epac1 in mediating the function of CD4+ CD25+ regulatory T-cells (Tregs), which are known suppressors of the adaptive and humoral immune responses. The suppressive potency of WT and Epac1 KO Tregs was examined using an in vitro assay that examines CD4+ CD25− (Tconv) proliferation in the presence Tregs. Epac1 KO Tconv and WT Tconv proliferated at the same rate when cultured alone. The addition of WT Tregs suppressed the proliferation of both cell populations to the same extent, while the addition of Epac1 KO Tregs suppressed the proliferation of Epac1 KO Tconv to a much lesser degree than it did WT Tconv's. To confirm the specificity of Epac1's impact on Tregs mediated suppression of Tconv, the suppression assay was repeated in the presence of ESI-09 and the outcome was similar. Taken together, these results suggest that presence of Epac1 in Tregs and Tconv sensitizes the latter to suppression by the former.

These findings show that EPAC1 antagonists are effective adjuvants and can be used in conjunction with vaccines and immune-modulators for immunotherapies. Such immunotherapies include those for cancer or other diseases. EPAC1 is a viable target for immune-modulation. In particular EPAC1 inhibitors, can be used as adjuvants for vaccines and/or modulators of immunotherapies.

Certain aspects are directed to administering to a subject an EPAC1 inhibitor in conjunction with an antigen. In certain aspects the EPAC1 inhibitor is administered before, during, or after administration of an antigen. In one embodiment, the antigen is a viral protein. In another embodiment, the antigen is a bacterial protein or a portion thereof. In yet another embodiment, the antigen is a mammalian protein or a portion thereof, e.g., a cancer antigen. The antigen can be administered 1, 2, 3, 4, 5, 6, 7, 8, 9, 10, 11, 12, 13, 14, 15, 16, 17, 18, 19, 20, 21, 22, 23, or 24 hours or days before or after EPAC inhibitor administration. The antigen and/or inhibitor can be administered 1, 2, 3, 4, 5, 6, 7, 8 or more times over various time periods. In certain aspects more than one antigen can be administered. In certain aspects the subject is a human subject. In a further embodiment additional immune modulators can be administered.

In certain aspects an EPAC inhibitor is administered in combination with an antibody therapy, which can enhance the efficacy of antibody therapy for treatment of cancer or infectious diseases. The EPAC inhibitor can be administered in combination with antibodies such as rituximab, herceptin or erbitux. In some embodiments, the antibody is an anti-cancer antibody. Monoclonal antibodies, including human and humanized monoclonal antibodies work by targeting tumor specific antigens, thus enhancing the host's immune response to tumor cells. Other antibody therapies include use of polyclonal antibodies and use of antibody fragments or regions. Examples of such therapies are trastuzumab (Herceptin), cetuximab, and rituximab (Rituxan or Mabthera).

Tumor-associated antigens that can be used in the methods of immune modulation include, but are not limited to, 707-AP, Annexin II, AFP, ART-4, BAGE, β-catenin/m, BCL-2, bcr-abl, bcr-abl p190, bcr-abl p210, BRCA-1, BRCA-2, CAMEL, CAP-1, CASP-8, CDC27/m, CDK-4/m, CEA (Huang et al. (2002) *Exper Rev. Vaccines* 1:49-63), CT9, CT10, Cyp-B, Dek-cain, DAM-6 (MAGE-B2), DAM-10 (MAGE-B1), EphA2 (Zantek et al. (1999) *Cell Growth Differ.* 10:629-38; Carles-Kinch et al. (2002) *Cancer Res.* 62:2840-7), ELF2M, ETV6-AML1, G250, GAGE-1, GAGE-2, GAGE-3, GAGE-4, GAGE-5, GAGE-6, GAGE-7B, GAGE-8, GnT-V, gp100, HAGE, HER2/neu, HLA-A*0201-R170I, HPV-E7, HSP70-2M, HST-2, hTERT, hTRT, iCE, inhibitors of apoptosis (e.g. survivin), KIAA0205, K-ras, LAGE, LAGE-1, LDLR/FUT, MAGE-1, MAGE-2, MAGE-3, MAGE-6, MAGE-A1, MAGE-A2, MAGE-A3, MAGE-A4, MAGE-A6, MAGE-A10, MAGE-A12, MAGE-B5, MAGE-B6, MAGE-C2, MAGE-C3, MAGE-D, MART-1, MART-1/Melan-A, MC1R, MDM-2, mesothelin, Myosin/m, MUC1, MUC2, MUM-1, MUM-2, MUM-3, neo-polyA polymerase, NA88-A, NY-ESO-1, NY-ESO-1a (CAG-3), PAGE-4, PAP, Proteinase 3 (Molldrem et al. (1996) *Blood* 88:2450-7; Molldrem et al. (1997) *Blood* 90:2529-34), P15, p190, Pm1/RARα, PRAME, PSA, PSM, PSMA, RAGE, RAS, RCAS1, RU1, RU2, SAGE, SART-1, SART-2, SART-3, SP 17, SPAS-1, TEL/AML 1, TPI/m, Tyrosinase, TARP, TRP-1 (gp75), TRP-2, TRP-2/INT2, WT-1, and alternatively translated NY-ESO-ORF2 and CAMEL proteins.

E. Anti-Infective

In certain aspects EPAC specific inhibitors can be used for attenuating or preventing uptake of a microbe by a vascular endothelial cell. Endothelial and epithelial cell—cell junctions and barriers play a critical role in the dissemination of microbe infection. EPAC and its down-stream effector Rap1 have been shown to play an important role in cellular functions related to endothelial cell junctions and barrier (Kooistra et al. (2005) *FEBS Lett* 579:4966-4972; Baumer et al. (2009) *J Cell Physiol.* 220:716-726; Noda et al. (2010) *Mol Biol Cell* 21:584-596; Rampersad et al. *J. Biol. Chem.* 285:33614-33622; Spindler et al (2011) *Am J Pathol* 178:2424-2436). In addition, EPAC is known to be involved in phagocytosis (Yeager et al (2009) *Infect Immun* 77:2530-2543; Shirshev (2011) *Biochemistry* (Mosc) 76:981-998).

Cyclic AMP is a universal second messenger that is evolutionally conserved in diverse form of lives, including human and pathogens such as bacterial, fungi and protozoa. It has been well recognized that cAMP play major roles in microbial virulence, ranging from a potent toxin to a master regulator of virulence gene expression. (MaDonough & Rodriguez (2012) *Nature Rev Microbiol* 10:27-38). As a major intracellular cAMP receptor, it is likely that EPAC proteins are important cellular targets for microbe infection.

To determine if EPAC 1 plays a role in rickettsia infection, WT and EPAC $1^{-/-}$ C57BL/6 mice were challenged with sublethal dose of *R. australia*. All WT mice became severely ill 5 days post infection and a few WT mice died. On the other hand, none of the EPAC1$^{-/-}$ mice became severely sick. These results suggest that deletion of EPAC1 protects mice from *R. australia* infection.

To test if EPAC inhibitors are capable of protecting mice from lethal-dose infection of *R. australia*. WT C57BL/6 mice were treated with vehicle or ESI-09 (10 mg/kg, IP) daily. Five days after the treatment, mice were challenged with lethal dose of *R. australia* and continued ESI-09 daily treatment. Similar to EPAC1 genetic deletion, pharmacological inhibition of EPAC1 also led to a striking protection of *R. australia* infection. 100% control group became severely sick while only 10% of the treatment group showed sign of sickness.

To investigate the mechanism of EPAC1 inhibition-mediated protection of *R. australia* infection, HUVEC cells treated with vehicle or ESI-09 were infected with *R. australia*. The number of intracellular *R. australia* was dramatically reduced in ESI-09 treated HUVEC cells. These data demonstrate that inhibition of EPAC by ESI-09 treatment suppresses cellular entry of *R. australia.*

Certain embodiments are directed to methods of suppressing microbe infection comprising administering an EPAC specific inhibitor to a subject having or under the risk of microbe infection. In certain aspects the microbe is a bacteria, virus, or fungi. In other aspects the EPAC specific inhibitor is selected from the EPAC inhibitors described herein.

F. Leptin Modulator

In certain aspects, compounds described herein can be used to enhance leptin sensitivity and reduce adiposity in a subject.

The adipocyte hormone leptin plays a central role in energy homeostasis. It was discovered in obese mice missing a serum factor, which when replaced decreased food intake and body weight (Zhang et al. (1994) *Nature* 372: 425-32). Because of these initial observations, much of the earlier therapeutic attempt using this hormone has been in the treatment of obesity. Serum leptin concentrations in the majority of humans with obesity are high, and a state of leptin resistance is thought to exist (Mantzoros et al. (2000) *J Clin Endocrinol Metab* 85:4000-4002). Thus far, the effect of recombinant human leptin has been limited in causing weight loss in obese individuals except in the state of congenital leptin deficiency (Heymsfield et al. (1999) *Jama* 282:1568-75; Farooqi et al. (1999) *N Engl J Med* 341:879-84).

Activation of EPAC has been shown to impair leptin signaling. Central infusion of an EPAC activator has been shown to blunt the anorexigenic actions of leptin (Fukuda et al. (2011) *Cell Metab* 13:331-339). The present invention provides for the use of EPAC modulators for the treatment of diseases related to abnormalities in the leptin pathway, such as obesity and lipoatrophy and its associated metabolic abnormalities (e.g., hyperglycemia, dyslipidemia, hyperlipidemia, hypercholesterolemia, hypertriglyceridemia, atherosclerosis, vascular restenosis, and insulin resistance).

Epac1 Knockout (KO) Mice Display Blunted Body Weight Gain. Global Epac1 knockout mice were generated using the Cre-loxP system. Epac1 null mutant mice in general appear healthy without any obvious physical abnormalities. They have similar body weights compared to wild-type mice at birth and up to three weeks of age, when the mice were weaned and started on the high fat diet or standard rodent chow. The body weight gain of Epac1 KO mice on standard chow diet slowed down and became significantly lower than that of the wild-type mice around week 5, eventually reaching approximately 85% of wild-type mice. Similar observations were made for the HFD-fed mice. The body weight of Epac1 KO mice became significantly lower around week 7, and maintained at about 90% of wild-type mice. The average daily food intake of Epac1 KO mice on chow diet was significantly lower than that of the wild-type. On the other hand, while the average daily food intake of Epac1 KO mice on HFD was lower than that of the wild-type mice on HFD, the difference was not statistically significant. Whole body micro-CT scans were performed on HFD-fed mice and body length was measured from C1 to L6 vertebrae to confirm that body weight gain lag in Epac1 KO mice is not the result of overall growth retardation.

Epac1 Deficiency Reduces Adiposity. To determine why body weight gain is reduced in Epac1 KO mice, the adiposity of the animals was examined. The epididymal fat pads from Epac1 KO mice were visually smaller and weighted significantly less than those from wild-type. When analyzed by Micro-CT imaging, the total fat mass of Epac1 null mice on HFD was significantly less than wild-type. This difference was significant even after fat mass was normalized to body weight. In fact, the difference in total fat mass was larger than the difference in body weight, suggesting that the reduced body weight of Epac1 KO mice is mainly due to a reduction in fat mass. A decrease in adipose tissue mass can be the result of impaired adipocyte differentiation, a reduction of adipocyte size, or both. Histological analysis of epididymal white fat tissue (EWAT) revealed that adipocytes from Epac1 null mice were much smaller than those from the wild-type counterparts. On the other hand, ex vivo adipocyte differentiation analyses using MEF cells isolated from both wild-type and Epac1 KO mice revealed that the Epac1 KO MEFs were as competent as wild-type MEFs to differentiate into adipocytes, suggesting that Epac1 deficiency did not impede normal adipogenesis.

Leptin is secreted by adipose tissue and the plasma levels of leptin are known to correlate with adipose tissue mass while plasma leptin falls in both humans and mice after weight loss (Considine et al. (1996) *N. Engl. J. Med.* 441 334:292-295; Friedman and Halaas (1998) *Nature* 395:763-770; Maffei et al. (1995) *Nat. Med.* 1:1155-1161). To investigate if a reduced fat mass is correlated with reduced plasma leptin in Epac1 null mice, the plasma leptin levels of Epac1 KO and wild-type mice on standard chow and HFD were compared, respectively. For mice on the standard chow diet, the average plasma leptin level of 16-week-old wild-type mice was around 3.97±0.78 ng/ml which is consistent with previous publications (Bates et al. (2003) *Nature* 421:856-859; Kievit et al. (2006) *Cell Metab* 4:123-132). However, the plasma leptin level of the age and gender matched Epac1 KO mice was significantly lower, at about 1.01±0.26 ng/ml. For the mice on HFD at 28-weeks of age (25 weeks on HFD), the average leptin concentration was about 83.16±5.76 ng/ml, whereas the average leptin level of Epac1 KO mice was about 66.15±3.52 ng/ml. These results corroborate the anatomical and morphological observation that Epac1 deficiency reduces white fat tissue adiposity in the standard chow diet as well as HFD fed mouse.

To determine if the apparent decreases in plasma leptin levels are merely the result of decreased adiposity, the leptin levels of 3-week-old mice were measured before significant body weight and adiposity difference can be observed between the wild-type and Epac1 mull mice. Leptin levels in Epac1 KO mice were already reduced significantly compared to those in age and gender match wild-type mice.

Loss of Epac1 Heightens Leptin Signaling Activity and Sensitivity In Vivo. In light of a recent finding by Fukuda, et al. that activation of Epac-RAP1 with Epac selective agonist, 8-pCPT-2'-O-Me-cAMP (8-(4-chlorophenylthio)-2'-O-methyladenosine-3',5'-cyclic mono-phosphorothioate) blunts leptin signaling in hypothalamus and causes central leptin resistance (Fukuda et al. (2011) *Cell Metab* 13:331-339), the pSTAT3 Y705 localization and immunoactivity in the arcuate nucleus (AN), with or without Epac1, was compared to determine the consequence of reduced plasma leptin levels associated with the loss of Epac1 on leptin sensitivity in vivo. The proopiomelanocortin neurons are direct targets of leptin in the hypothalamus and the leptin-induced STAT3 Y705 phosphorylation and nuclear translocation in the AN is involved in body weight regulation (Bates et al. (2003) *Nature* 421:856-859; Cheung et al. (1997) *Endocrinology* 138:4489-4492; Hubschle et al. (2001) *J. Neurosci.* 21:2413-2424; Schwartz et al. (1996) *J. Clin. Invest* 98:1101-1106). The Epac1 KO AN tissue displayed a slightly enhanced baseline level (PBS vehicle injection) of pSTAT3 Y705 immunoractivity, and a markedly increased nuclear immunostaining of pSTAT3 Y705 in response to ICV injection of leptin than that of the wild-type. To further compare the total pSTAT3 Y705 in the hypothalamus upon stimulation with leptin, we repeated ICV leptin injections and excised the hypothalami for immunoblotting analysis. Consistent with our immunofluorescence study, the basal and the stimulated levels of pSTAT3 Y705 were both increased in the Epac1 KO hypothalamic tissue, suggesting that loss of Epac1 enhances central leptin signaling and sensitivity while decreases peripheral (plasma) leptin levels in vivo.

To investigate if this increased leptin sensitivity associated with loss of Epac1 translates into decreased food intake and body weight in response to leptin in vivo, leptin was injected intraperitoneally to 20-week-old mice. The mice were individually housed for one week to acclimate them with the environment. Escalation of leptin was utilized to cover a wide range of doses (Heymsfield et al. (1999) *JAMA* 282:1568-1575). Due to the nocturnal activity of mice and the short half-life of leptin (Ahren et al. (2000) *Int. J. Obes. Relat Metab Disord.* 24:1579-1585; Hill et al. (1998) *Int. J. Obes. Relat Metab Disord.* 22:765-770), food intake was measured during the first 4-hours of the dark cycle, food intake during the entire 24-hour period, and body weight at the beginning of each dark cycle. It was found that food intake over the first four hours of the dark cycle decreased in a dose-dependent manner in response to leptin administration. Epac1 KO mice displayed a significant reduction in food intake at the higher doses of leptin versus wild-type mice during the first 4-hour dark cycle. Although the 24-hour food intake also decreased with leptin administration, the magnitude of decrease was not statistically significant. Interestingly, leptin injection induced a transient body weight decrease in the wild-type mice which recovered quickly even with highest dose of leptin. In contrast, leptin induced a persistent and dose-dependent body weight reduction in Epac1 KO mice. These results demonstrate that Epac1 deficiency enhances leptin signaling in hypothalamus and that Epac1 KO mice are more sensitive to leptin treatment in vivo in regard to the reduction of food intake and body weight.

To explore the feasibility of increasing leptin sensitivity by targeting Epac1 using small molecules, organotypic brain slice cultures were prepared from 11-day old wild-type C57BL/6 mice. After 7 days ex vivo culture, treatment of the brain tissue with the Epac specific antagonist ESI-09 led to an enhanced pSTAT3 Y705 level both at the basal state and in response to leptin stimulation. Moreover, Epac specific inhibitors also increased the cellular level of SHP2 as observed in the Epac1 KO mice. These pharmacological data are in agreement with results obtained using Epac1 KO mice and further confirm that inhibition of Epac1 enhances leptin signaling in the hypothalamus. To further investigate the therapeutic potential of this small molecule, wild-type mice were with ESI-09 (50 mg/kg) or vehicle (corn oil) by oral gavage for 3 weeks. Plasma leptin was significantly reduced after ESI-09 relative to vehicle treatment.

Epac1 KO Mice are Protected Against HFD Induced Glucose Intolerance. It has been well documented that enhanced leptin sensitivity confers resistance to HFD-induced obesity and improved glucose tolerance (Berglund et al. (2012) *J. Clin. Invest* 122:1000-1009; Howard et al. (2004) *Nat. Med.* 10:734-738; Kievit et al. (2006) *Cell Metab* 4:123-132; Mori (2004) *Nat. Med.* 522 10:739-743). The glucose handling capability of wild-type and Epac1 KO mice were compared using the oral glucose tolerance test (OGTT). While similar OGTT results were obtained for wild-type and Epac1 KO mice on the standard chow diet, the Epac1 KO mice displayed a markedly enhanced glucose handling capability after 15 weeks on HFD. Firstly, the fasting glucose levels of HFD Epac1 KO mice were significantly lower than those of wild-type; secondly, Epac1 KO mice cleared glucose from blood significantly faster than wild-type mice at every time point after glucose administration. The blood glucose levels of Epac1 KO mice dropped back to baseline in 2 hours while the wild-type blood glucose levels remained elevated. In parallel, insulin levels were monitored after overnight fasting and 15 min after glucose administration. No significant differences were observed between wild-type and Epac1 KO mice on the standard chow diet: both showed similar low fasting insulin levels that increased to a similar extent in response to glucose challenge. On the other hand, while HFD Epac KO mice showed a slightly decreased fasting insulin level, both HFD wild-type and Epac1 KO mice maintained the ability to increasing plasma insulin in response to blood glucose concentration elevation. These data suggest that Epac1 KO mice are resistant to HFD-induced insulin insensitivity as in the case of the wild-type mice. These studies show that Epac1 KO mutant mice are largely protected from the HFD-induced glucose intolerance and insulin resistance.

In certain aspects, an EPAC inhibitor is administered to a leptin-resistant subject. The administration of an EPAC inhibitor increases sensitivity of the subject to endogenous leptin. In a further aspect, leptin or leptin analog can be administered in combination with an EPAC inhibitor to overcome leptin resistance or deficiency. In another aspect, an overweight subject is administered an EPAC inhibitor reducing body weight of the subject. In yet another aspect, an EPAC inhibitor is administered to increase systemic insulin sensitivity. Other aspects include administering an EPAC activator to a subject having anorexic or cachexic symptoms or syndromes, or a hypersensitivity to leptin.

II. Chemical Definitions

Various chemical definitions related to EPAC modulating compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer. In certain aspects, one, both, or the predominant enantiomer forms or isomers are all covered.

As used herein, the term "nitro" means —$NO_2$; the term "halo" or "halogen" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear (i.e., unbranched) or branched carbon chain of 1, 2, 3, 4, 5, 6, 7, 8, 9, or 10 carbons, which may be fully saturated, monounsaturated, or polyunsaturated. An unsaturated alkyl group includes those having one or more carbon-carbon double bonds (alkenyl) and those having one or more carbon-carbon triple bonds (alkynyl). The groups, —$CH_3$ (Me, methyl), —$CH_2CH_3$ (Et, ethyl), —$CH_2CH_2CH_3$ (n-Pr, n-propyl), —$CH(CH_3)_2$ (iso-Pr, iso-propyl), —$CH_2CH_2CH_2CH_3$ (n-Bu, n-butyl), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, S, and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, —$CH_2CH_2OC(O)CH_3$, —$CH_2CH_2NHCO_2C(CH_3)_3$, and —$CH_2Si(CH_3)_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule. Examples of cycloalkyl groups include cyclopropyl, cyclobutyl, cyclopentyl, cyclohexyl, and cycloheptyl groups. Examples of heterocyclic groups include indole, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, and the like.

The term "aryl" includes, but is not limited to phenyl, α-naphthyl, β-naphthyl, biphenyl, anthryl, tetrahydronaphthyl, fluorenyl, indanyl, biphenylenyl, and acenaphthenyl. In certain aspects an aryl group is a phenyl group. Specifically included within the definition of "aryl" are those aromatic groups that are optionally substituted. For example, in some embodiments of the present invention, the "aryl" groups are optionally substituted with from 1 to 5 substituents selected from the group consisting of hydrogen, hydroxy, aryl, acyl, C1-C6 alkyl, C1-C6 alkoxy, C2-C6 alkenyl, C2-C6 alkynyl, substituted alkyl, substituted alkoxy, substituted alkenyl, substituted alkynyl, amino, amino substituted by one or two C1-C6 alkyl groups, cyano, halogen, nitro, and trihalomethyl. In some embodiments of the present invention, for example, in some embodiments wherein the ary group is phenyl, the aryl groups are optionally substituted with from 1 to 5 substituents selected from the group consisting of hydrogen, hydroxy, aryl, acyl, C1-C6 alkoxy, C2-C6 alkenyl, C2-C6 alkynyl, substituted alkyl, substituted alkoxy, substituted alkenyl, substituted alkynyl, amino, amino substituted by one or two C1-C6 alkyl groups, cyano, halogen, nitro, and trihalomethyl.

The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 4-azaindole, 5-azaindole, 6-azaindole, 7-azaindole, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: CF, $CF_3O$, halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, cycloalkyl, heterocyclyl, aryl, and heteroaryl. In certain aspects the substituents may be further substituted with one or more substituents independently selected from: halogen, nitro, cyano, hydroxy, amino, mercapto, formyl, carboxy, carbamoyl, alkyl, heteroalkyl, alkoxy, alkylthio, alkylamino, (alkyl)$_2$amino, alkylsulfinyl, alkylsulfonyl, arylsulfonyl, cycloalkyl, heterocyclyl, aryl, or heteroaryl.

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means oxygen that is double bonded to a carbon atom.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base, such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the three dimensional configuration of those atoms differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

III. Pharmaceutical Formulations and Administration

In certain embodiments, the invention also provides compositions comprising one or more EPAC modulator with one or more of the following: a pharmaceutically acceptable diluent; a carrier; a solubilizer; an emulsifier; a preservative; and/or an adjuvant. Such compositions may contain an effective amount of at least one EPAC modulator. Thus, the use of one or more EPAC modulators as provided herein for the preparation of a medicament is also included. Such compositions can be used in the treatment of a variety of EPAC associated diseases or conditions such as cancer or leptin associated disease or conditions.

An EPAC modulator may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the EPAC modulating agents, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to an organ or a tumor is also contemplated by the present invention. When administering the compositions by injection, the administration may be by continuous infusion or by single or multiple boluses. For parenteral administration, the EPAC modulating agents may be administered in a pyrogen-free, parenterally acceptable aqueous solution comprising the desired EPAC modulating agents in a pharmaceutically acceptable vehicle. A particularly suitable vehicle for parenteral injection is sterile distilled water in which one or more EPAC modulating agents are formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

To determine the bioavailability of EPAC inhibitors, an IP injection formulation was developed in which the compounds were dissolved in ethanol and then diluted 1:10 with a 10% Tween 80 in normal saline solution. This formulation was determined suitable by passing the simulated in vivo blood dilution assay. In vivo pharmacokinetic studies were performed in four week old female C57BL6/N mice. Following one single intraperitoneal (IP) injection of the ESI-09 compound (10 mg/kg) in mice (n=5 for each time point), blood levels of ESI-09 were determined to be rapidly elevated reaching maximal values of 42,520 ng/ml (128 M) at 0.5 hr with a half-life of 3.5 hrs. These results suggest that ESI-09 has an excellent bioactivity in vivo.

For the compounds of the present invention, alone or as part of a pharmaceutical composition, such doses are between about 0.001 mg/kg and 1 mg/kg body weight, preferably between about 1 and 100 µg/kg body weight, most preferably between 1 and 10 µg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

In some methods of the invention, an EPAC inhibitor is administered to a cancer cell. The cancer cell may be in a patient and the patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods of the invention. It is specifically contemplated that any of the compounds or derivatives or analogs, can be used with these combination therapies.

IV. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

A. Results and Discussion

1. Chemistry

Figure 1B:
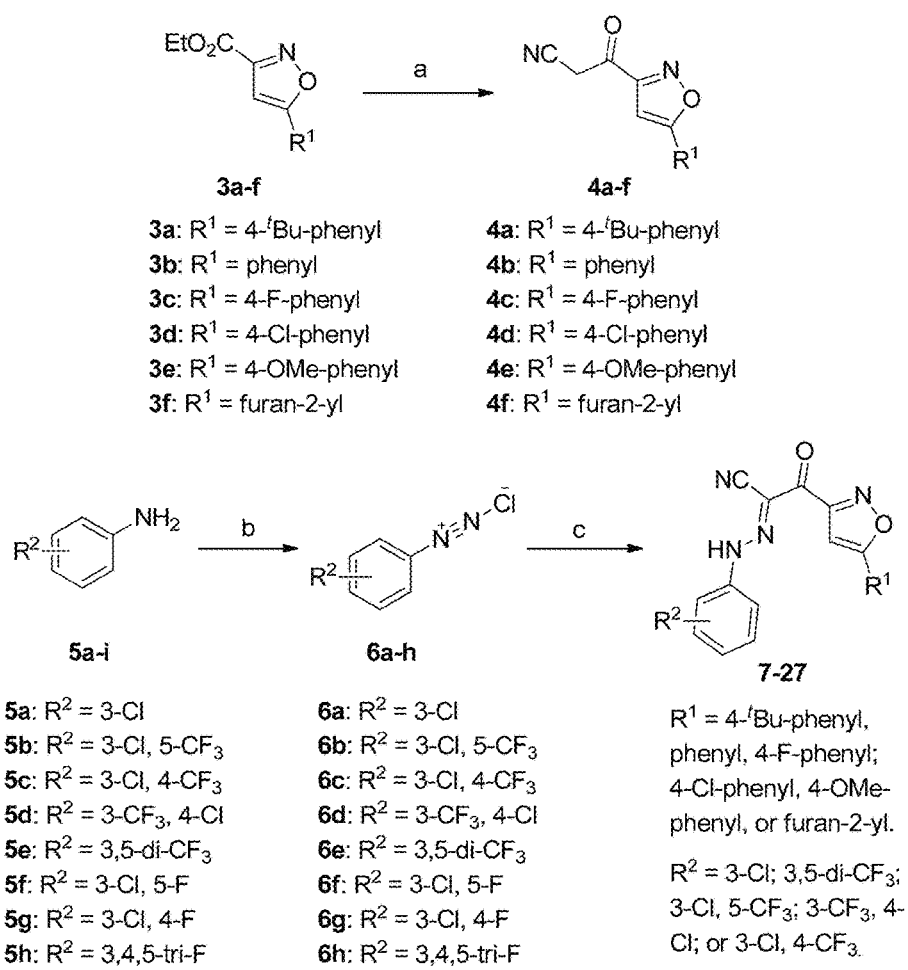
Figure 1C:
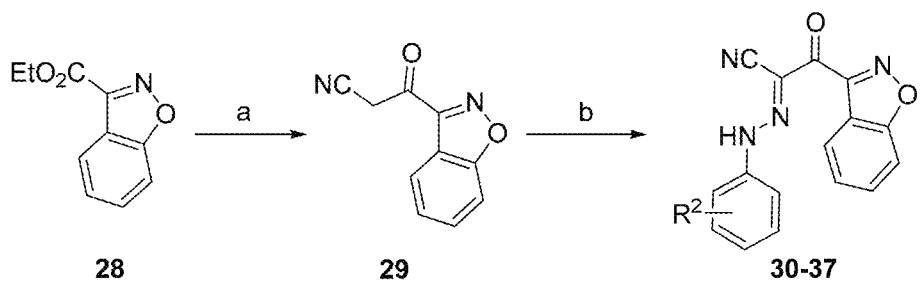

The synthesis of new derivatives based on 2-(isoxazol-3-yl)-2-oxo-N'-phenyl-acetohydrazon-oyl cyanide scaffold with chemical optimizations of 5-tert-butyl group on the isoxazole is outlined in Scheme 1 (FIG. 1B). Various ethyl isoxazole-3-carboxylates 3a-f were used as the key intermediates. 3a-f were prepared either from the commercially available pinacolones and oxalic acid diethyl esters in two steps as previously described (Chen et al., *Tetrahedron Lett.* (2013) 54:1546-49; Ye et al., *J. Med. Chem.* (2015) 58:6033-47), or from ethyl esterification of the commercially available isoxazole-3-carboxylic acids. Ethyl esters 3a-f were first converted into the corresponding ketonitriles 4a-f by the treatment of MeLi and $CH_3CN$ using our previously reported protocols (Chen et al., *Tetrahedron Lett.* (2013) 54:1546-49; Wild et al., *ACS Med. Chem. Lett.* (2016) 7:460-64). By further modifications of Kowalsko's reaction, NaH was used instead of MeLi as the base under a milder condition to generate the corresponding ketonitriles from ethyl esters 3a-f in good yields. On the other hand, aromatic amines 5a-h were treated with sodium nitrite and 2 N hydrochloric acid to give the corresponding aryldiazonium chlorides 6a-h. The aryldiazonium salts 6a-h with the crude cyanomethyl ketones 4a-f were then directly coupled in the presence of NaOAc as the catalyst at 0° C. afforded new derivatives of series I compounds 7-27 in 14-81% yields for two steps from 4a-f (Scheme 1, FIG. 1B). The desired products of series II 30-37 were accomplished from the commercially available ethyl benzo[d]isoxazole-3-carboxylate 28 with two steps in a similar fashion to those described for the synthesis of Series I.

2. Biology

In Vitro Evaluation of EPAC1 Inhibition. To explore the SARs and examine how the modifications on the isoxazole ring affect biological activities of newly synthesized analogues, we first evaluated their ability to inhibit EPAC1-mediated Rap1b-bGDP exchange activity using purified recombinant full-length EPAC1 proteins. Previous hit 1 was used as the reference compound, with an $IC_{50}$ value of 10.8 µM in inhibiting EPAC1 (Zhu et al., *Sci. Rep.* (2015) 5:9344).

Figure 2:
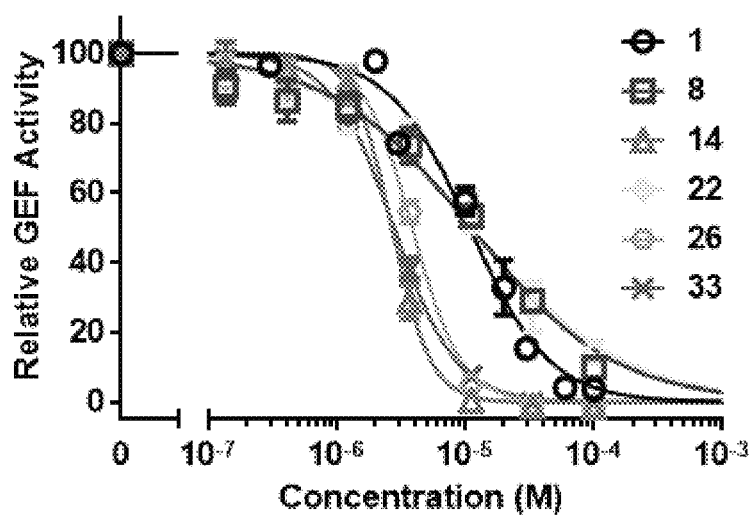
FIG. 2. Relative inhibitory activity for EPAC1-mediated Rap1b-bGDP exchange. Dose-dependent inhibition of EPAC1 GEF activity by compound 1 (black), 8 (blue), 14 (red), 22 (green), 26 (brown) and 33 (purple), in the presence of 20 µM cAMP. Relative GEF activity were presented as normalized reaction rate constant (means±SEM, n=3) described in the method.

As shown in Table 1, we initially investigated the effect of the inserted phenyl ring between 5-tert-butyl group and isoxazole ring A of hit 1 in series I, leading to compound 7 with an $IC_{50}$ value of 8.6 µM, which has a slight increase of inhibitory activity in comparison with that of 1. Given that fluorine substitutions may have an important contribution to the improvement of metabolic stability, solubility and bioactivity, as found in our previous publications (Ye et al., *J. Med. Chem.* (2015) 58:6033-47; Ye et al., *J. Med. Chem.* (2013) 56:2885-903), selected fluorine substitutions on B ring were introduced to newly designed compounds 8-11. 3,5-di-$CF_3$-substituted analogue 11 results in a slight loss of activity, while compound 10 with 3-$CF_3$,4-Cl-substitution displays an enhanced potency, with an $IC_{50}$ value of 7.3 µM. To evaluate the importance of 4-tert-butyl group on the inserted phenyl ring, we attempted the removal of this moiety, leading to new analogues 13-15. Compounds 13-15, not only have a better solubility than previously reported compound 12 (Ye et al., *J. Med. Chem.* (2015) 58:6033-47), but also exhibit an improved potency compared to that of 4-$^t$Bu-phenyl substituted analogues. This indicates that 4-$^t$Bu group on the inserted phenyl ring is dispensable for its activity. The most potent one of this series, 3-$CF_3$,4-Cl-substituted compound 14, is about 5-fold increase in potency when compared to that of 1, with an $IC_{50}$ value of 2.4 µM (FIG. 2). The inventors next explored the electronic effect of substitutions at the 4-position of the inserted phenyl ring. Compounds 16-24 all result in a loss of activity. However, compounds 22-24 with other electron-donating groups such as methoxy, are more potent than corresponding compounds 16-21 with other electron-withdrawing groups such as fluoro and chloro. Particularly, 4-methoxy substituted analogues 23 and 24 display good activities, with the same $IC_{50}$ values of 5.6 µM. As expected, replacement of 4-methoxy phenyl on the isoxazole ring A with its bioisostere, more electron-donating furan-2-yl group (as in compounds 25-27), also leads to an increase of activity. The most potent one of them, 25, shows an $IC_{50}$ value of 3.6 µM. These results suggest that the 5-position of the isoxazole ring A is more suitable for chemical modifications and favorable with electron-donating groups.

In series II as shown in Table 2, replacement of isoxazole ring A of 1 with benzo[d]isoxazol moiety (as in compound 30), results in a slight loss of potency when compared to that of 1, with an $IC_{50}$ value of 13.2 µM. However, further installation of fluorine-containing groups on its B ring quickly boosts the activity, except 3-Cl,5-F and 3,4,5-tri-F groups (as in compounds 34 and 37). Compounds 31-33 result in approximately 2-4-fold increase in potency when compared to that of 1, with $IC_{50}$ values of about 2-4 µM (FIG. 2).

All these findings suggest that the isoxazole ring A of 1 can tolerate chemical modifications with either introduction of electron-donating substitutions or restrictedly fusing with a phenyl ring.

TABLE 1

Apparent $IC_{50}$ values of substituted 2-(isoxazol-3-yl)-2-oxo-N'-phenyl-acetohydrazonoyl cyanide scaffolds for inhibiting EPAC1 GEF activity.

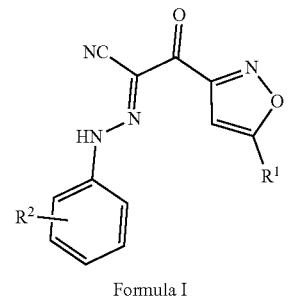

Formula I

| Compound | Code | $R^1$ | $R^2$ | Rap 1b-bGDP EPAC1 $IC_{50}$ (µM)[a] |
|---|---|---|---|---|
| 1 | ESI-09 | | | 10.8 ± 1.6 |
| 7 | NY0613 | 4-$^t$Bu-phenyl | 3-Cl | 8.6 ± 2.8 |
| 8 | NY0615 | 4-$^t$Bu-phenyl | 3-Cl, 5-$CF_3$ | 10.2 ± 2.7 |
| 9 | NY0616 | 4-$^t$Bu-phenyl | 3-Cl, 4-$CF_3$ | 9.0 ± 3.9 |
| 10 | NY0617 | 4-$^t$Bu-phenyl | 3-$CF_3$, 4-Cl | 7.3 ± 2.3 |
| 11 | NY0618 | 4-$^t$Bu-phenyl | 3, 5-di-$CF_3$ | 11.9 ± 6.0 |
| 12 | NY0395 | Phenyl | 3-Cl | >150 |
| 13 | NY0402 | Phenyl | 3-Cl, 5-$CF_3$ | 9.5 ± 1.2 |
| 14 | NY0460 | Phenyl | 3-$CF_3$, 4-Cl | 2.4 ± 0.2 |
| 15 | NY0457 | Phenyl | 3, 5-di-$CF_3$ | 7.2 ± 0.7 |
| 16 | NY0538 | 4-F-phenyl | 3-Cl | 38.6 ± 7.7 |
| 17a | NY0540 | 4-F-phenyl | 3-Cl, 5-$CF_3$ | 12.7 ± 1.1 |
| 17b | NY0541 | 4-F-phenyl | 3-Cl, 4-$CF_3$ | 5.1 ± 0.3 |
| 18 | NY0542 | 4-F-phenyl | 3-$CF_3$, 4-Cl | 10.2 ± 0.8 |
| 19 | NY0641 | 4-Cl-phenyl | 3-Cl | 77.6 ± 35.8 |
| 20 | NY0642 | 4-Cl-phenyl | 3-$CF_3$, 4-Cl | 7.8 ± 2.1 |
| 21 | NY0643 | 4-Cl-phenyl | 3, 5-di-$CF_3$ | 11.4 ± 2.7 |
| 22 | NY0653 | 4-OMe-phenyl | 3-Cl | 11.4 ± 2.8 |
| 23 | NY0654 | 4-OMe-phenyl | 3-$CF_3$, 4-Cl | 5.6 ± 1.1 |
| 24 | NY0655 | 4-OMe-phenyl | 3, 5-di-$CF_3$ | 5.6 ± 1.0 |
| 25 | NY0724 | furan-2-yl | 3-Cl | 9.9 ± 3.3 |
| 26 | NY0725 | furan-2-yl | 3-Cl, 5-$CF_3$ | 3.6 ± 0.2 |
| 27 | NY0726 | furan-2-yl | 3-$CF_3$, 4-Cl | 4.2 ± 0.9 |

[a]The values are the mean ± SE of at least three independent experiments.

TABLE 2

Apparent IC$_{50}$ values of substituted 2-(isoxazol-3-yl)-2-oxo-N'-phenyl-acetohydrazonoyl cyanide scaffolds for inhibiting EPAC1 GEF activity.

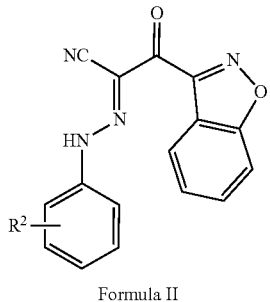

Formula II

| Compound | Code | R² | Rap 1b-bGDP EPAC1 IC$_{50}$ (μM)$^a$ |
|---|---|---|---|
| 30 | NY0491 | 3-Cl | 13.2 ± 3.6 |
| 31 | NY0495 | 3-Cl, 5-CF$_3$ | 4.6 ± 0.8 |
| 32 | NY0561 | 3-Cl, 4-CF$_3$ | 3.0 ± 0.3 |
| 33 | NY0562 | 3-CF$_3$, 4-Cl | 2.7 ± 0.3 |
| 34 | NY0496 | 3-Cl, 5-F | 18.9 ± 4.9 |
| 35 | NY0564 | 3-Cl, 4-F | 8.5 ± 3.5 |
| 36 | NY0563 | 3,5-di-CF3 | 6.7 ± 0.7 |
| 37 | NY0494 | 3,4,5-tri-F | 13.1 ± 2.5 |

$^a$The values are the mean ± SE of at least three independent experiments.

Figure 3:
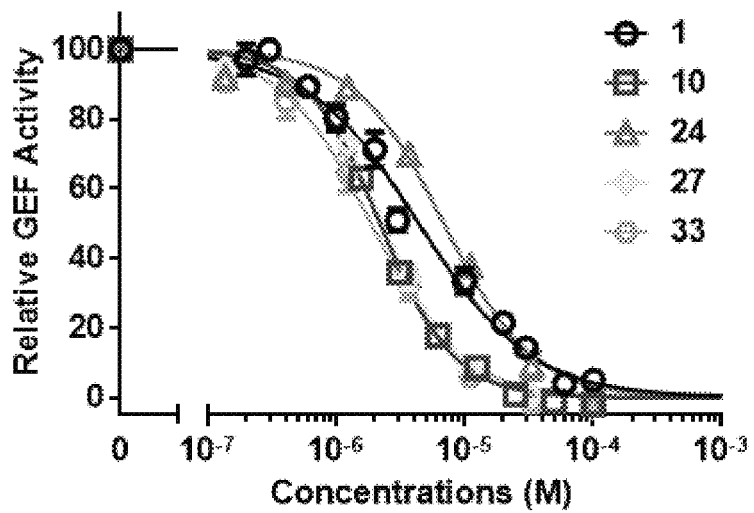
FIG. 3. Relative inhibitory activity for EPAC2-mediated Rap1b-bGDP exchange. Dose-dependent inhibition of EPAC2 GEF activity by compound 1 (black), 10 (blue), 24 (red), 27 (green), 33 (brown), in the presence of 20 µM cAMP. Relative GEF activity were presented as normalized reaction rate constant (means±SEM, n=3) described in the method.

In Vitro Evaluation of EPAC2 Inhibition. From the biological results discussed above, compounds 10, 14-15, 23-24, 26-27, and 31-32 were identified as potent EPAC1 inhibitors with IC$_{50}$ values lower than 8 μM and more potent than reference compound 1. Therefore, these selected compounds together with hit 1 were further evaluated for their ability to inhibit EPAC2-mediated Rap1b-bGDP exchange activity. As shown in Table 3, the previous hit 1 is 2.5-fold more potent on EPAC2 inhibition than that on EPAC1, with an IC$_{50}$ value of 4.4 μM. Interestingly, almost all of our selected, newly synthesized analogues exhibit significantly enhanced potency compared to that of 1, except compounds 23 and 24 (FIG. 3). Among these, compound 33 exhibits the best inhibitory activity for EPAC2, with an IC$_{50}$ value of 1.9 μM (FIG. 3). Compounds such as 14, 26 and 32-33 with IC$_{50}$ values lower than 4 μM for both EPAC1 and EPAC2 may serve as valuable pharmacological tools to probe the functions of EPAC in diseases or as potential drug candidates for further preclinical development.

TABLE 3

Apparent IC$_{50}$ values of substituted 2-(isoxazol-3-yl)-2-oxo-N'-phenyl-acetohydrazonoyl cyanide scaffolds for inhibiting EPAC2 GEF activity.

| Compound | Code | Rap1b-bGDP EPAC2 IC$_{50}$ (μM)$^a$ |
|---|---|---|
| 1 | ESI-09 | 4.4 ± 0.5 |
| 10 | NY0617 | 2.2 ± 0.3 |
| 14 | NY0460 | 2.3 ± 0.5 |
| 15 | NY0457 | 3.3 ± 0.8 |
| 23 | NY0654 | 4.5 ± 1.0 |
| 24 | NY0655 | 7.0 ± 0.9 |
| 26 | NY0725 | 2.2 ± 0.3 |
| 27 | NY0726 | 2.3 ± 0.2 |
| 31 | NY0495 | 2.2 ± 0.2 |
| 32 | NY0561 | 2.2 ± 0.4 |
| 33 | NY0562 | 1.9 ± 0.3 |

$^a$The values are the mean ± SE of at least three independent experiments.

Figure 4:
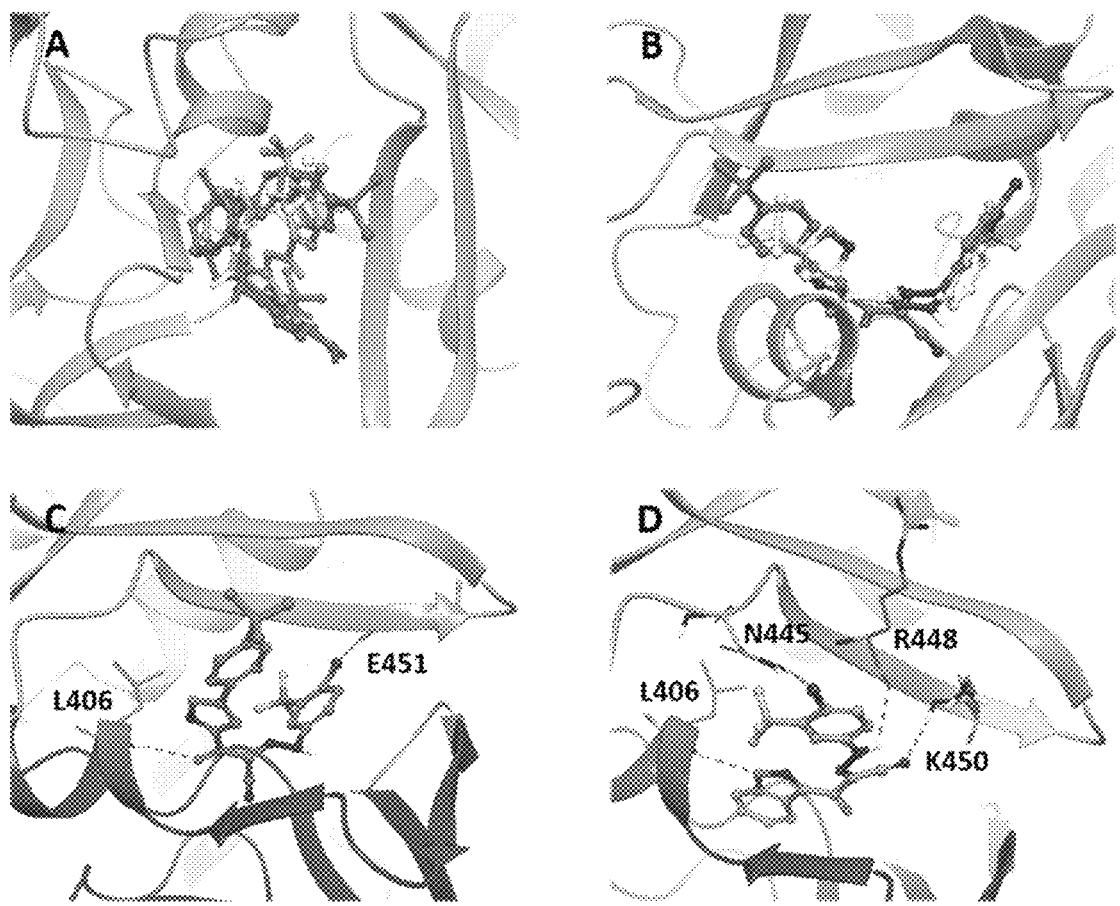
FIG. 4. (A) Overlay analysis of molecular docking poses of 1, 10 and 33 binding at the cAMP binding domain B (CBD-B) of EPAC2 protein (PDB Code $3CF_6$). cAMP is shown in red, 1 in yellow, 10 in magenta, and 33 in green. (B) Overlay of molecular docking poses of 1 (yellow) and 10 (magenta) binding at the CBD-B of EPAC2. (C) Predicted binding mode of 10 docked into the CBD-B of EPAC2. 10 is shown in magenta ball and stick representation. Key residues are displayed in sticks. Hydrogen bonds and halogen bond are shown in dotted purple lines. (D) Predicted binding mode of 33 docked into the CBD-B of EPAC2. 33 is shown in green ball and stick representation. Key residues are displayed in sticks. Hydrogen bonds and halogen bond are shown in dotted purple lines.

Predicted Binding Modes of Compounds 10 and 33 with the cAMP Binding Domain B (CBD-B) of EPAC2 Proteins. Due to the lack of the X-ray cocrystal structures of our newly synthesized small molecules and their targeted proteins, molecular docking studies as useful methods may help us better understand the structure—activity relationships of these new compounds toward EPACs. Given the only available X-ray crystal structures of inactive and active EPAC2 proteins (Rehmann et al., Nature (2006) 439:625-28; Rehmann et al., Nature (2008) 455:124-27), molecular docking studies of compounds 1, 10 and 33 at CBD-B of active EPAC2 protein (PDB Code 3CF6) were performed to investigate the predicted binding modes using the Schrödinger Small-Molecule Drug Discovery Suite (Wild et al., ACS Med. Chem. Lett. (2016) 7:460-64). Although this algorithm slightly differs from our previously employed AutoDock Vina (Chen et al., J. Med. Chem. (2014) 57:3651-65; Ye et al., J. Med. Chem. (2015) 58:6033-47), the docking results are generally consistent with the previous studies. The current docking results also reveal that these new compounds fit well into the functional CBD-B binding pocket of active EPAC2 (FIG. 4A). As shown in FIG. 4B, the molecular docking studies of 10 comply with previous results with hit 1 through the overlay analysis of two ligands. The isoxazolyl moiety and the 3-CF$_3$-4-Cl-phenyl fragment of 10 respectively extend to two previously supposed hydrophobic pockets, while this binding mode is further stabilized by the occurrence of one hydrogen bond between the oxygen atom in carbonyl group of the linker and residue L406, as well as one halogen bond between the chloro atom in the 3-CF$_3$-4-Cl-phenyl fragment and residue E451 (FIG. 4C). Interestingly, compound 33 interacts with EPAC2 protein in a substantially different manner from that of compounds 1 and 10 (FIGS. 4A and 4D). Its interactions with EPAC2 are dominated by the three strong hydrogen bonds and one halogen bond, including the oxygen atom in the benzo[d]isoxazol moiety with residue L406, the chloro group in phenyl fragment with residue N445, and the nitrogen atom in cyano group of the linker with K450 as well as its hydrogen atom with R448, in addition to the aforementioned hydrophobic interactions. These molecular docking studies could also reasonably explain why these two series of compounds with unique linkers might have better EPAC2 inhibitory activity (FIGS. 4C and 4D). It is worth mentioning that this new scaffold as in compound 33, where the nitrogen atom on the heteroaryl ring forms a hydrogen bond with residue L406, may offer a good starting point for further drug design and structural optimizations.

Two series of novel EPAC antagonists based on the scaffold of the previously identified high-throughput hit 1 (ESI-09) have been designed, synthesized, and biologically evaluated for their EPAC1 and EPAC2 inhibitory activities. The SAR results based on EPAC2 activity comply with our docking studies in general, indicating that the isoxazole ring B of 1 can tolerate chemical modifications with either introduction of flexible electron-donating substitutions or structurally restrictedly fusing with a phenyl ring. The new scaffold of series II, as in compound 33 interacting with EPAC2 in a novel binding mode, may offer a good starting point for further drug design and structural optimizations. All these modification efforts allow us to further tune the original hit 1 to achieve more potent and structurally diverse EPAC1 and EPAC2 inhibitors, such as 10 (NY0617), 14 (NY0460), 17b (NY0541), 26 (NY0725), 32 (NY0561), and 33 (NY0562) with $IC_{50}$ values in the low micromolar range. These compounds may hold promise as potential drug candidates toward novel therapeutics against human diseases, and serve as valuable pharmacological probes to elucidate the physiological functions of EPAC proteins. Further systematic optimizations based upon identified scaffolds of these two series toward EPAC subtype selectivity are under way and will be reported in due course.

B. Experimental Section

1. Chemistry

All commercially available starting materials and solvents were reagent grade, and used without further purification. Reactions were performed under a nitrogen atmosphere in dry glassware with magnetic stirring. Preparative column chromatography was performed using silica gel 60, particle size 0.063-0.200 mm (70-230 mesh, flash). Analytical TLC was carried out employing silica gel 60 F254 plates (Merck, Darmstadt). Visualization of the developed chromatograms was performed with detection by UV (254 nm). NMR spectra were recorded on a Bruker-600 or Bruker-300 ($^1$H, 600 & 300 MHz; $^{13}$C, 150 & 75 MHz) spectrometer. $^1$H and $^{13}$C NMR spectra were recorded with TMS as an internal reference. Chemical shifts were expressed in ppm, and J values were given in Hz. High-resolution mass spectra (HRMS) were obtained from Thermo Fisher LTQ Orbitrap Elite mass spectrometer. Parameters include the following: Nano ESI spray voltage was 1.8 kV; Capillary temperature was 275° C. and the resolution was 60,000; Ionization was achieved by positive mode. Melting points were measured on a Thermo Scientific Electrothermal Digital Melting Point Apparatus and uncorrected. Purities of final compounds were established by analytical HPLC, which was carried out on a Shimadzu HPLC system (model: CBM-20A LC-20AD SPD-20A UV/VIS). HPLC analysis conditions: Waters µBondapak C18 (300×3.9 mm); flow rate 0.5 mL/min; UV detection at 270 and 254 nm; linear gradient from 10% acetonitrile in water to 100% acetonitrile in water in 20 min followed by 30 min of the last-named solvent (0.1% TFA was added into both acetonitrile and water). All biologically evaluated compounds are >95% pure.

N-(3-Chlorophenyl)-2-(5-(4-(tert-butyl)phenyl)isoxazol-3-yl)-2-oxoacetohydrazonoyl cyanide (7). To a solution of $CH_3CN$ (0.43 mL, 7.32 mmol) in anhydrous THF (10 mL) was added 1.6 M methyl lithium in diethyl ether (2.30 mL, 3.66 mmol) at −78° C. under nitrogen. The mixture was stirred at −78° C. for 0.5 h, and ethyl 5-(4-(tert-butyl)phenyl)isoxazole-3-carboxylate 3a (0.50 g, 1.83 mmol) in THF (10 mL) was then added dropwise. The solution was stirred at −78° C. for 1 h and then quenched with acetic acid (0.21 mL, 3.66 mmol). The mixture was warmed to 0° C. and poured onto ice/water (10 mL) and extracted with ethyl acetate (20 mL). The organic lay was dried over $Na_2SO_4$, filtered and concentrated under reduced pressure. The crude residue 4a (330 mg, 75%) was obtained as a white solid and directly used for next step without further purification. $^1$H NMR (300 MHz, $CDCl_3$) δ 7.74 (d, J=8.4 Hz, 2H), 7.53 (d, J=8.4 Hz, 2H), 6.92 (s, 1H), 4.25 (s, 2H), 1.32 (s, 9H).

To a solution of 3-chloroaniline 5a (37 mg, 0.33 mmol) in $H_2O$ (10 mL cooled to −5° C.) was added 0.2 mL of 2 N HCl (aq.). To the resulting acidic aniline solution, 1 N solution of sodium nitrite (0.33 mL, 0.33 mmol) was added dropwise to generate the aryldiazonium salt solution 6a. To the aryldiazonium salt solution was added sodium acetate (54 mg, 0.66 mmol), followed by 1 mL solution of crude 3-oxo-3-(3-phenylisoxazol-5-yl)propanenitrile 4a (88 mg, 0.33 mmol) in ethanol. The reaction mixture was stirred at 0° C. for 5 min, and then poured onto $H_2O$ (10 mL) and extracted with ethyl acetate (20 mL). The organic layer was dried over $Na_2SO_4$, filtered and concentrated under reduced pressure. The residue was purified by short column chromatography on silica gel, eluting with hexane/ethyl acetate (2/1) to provide the desired product 7 (67 mg, 50% for two steps from 3a) as a yellow solid. $^1$H NMR (300 MHz, DMSO-$d_6$) δ 7.90 (d, J=8.4 Hz, 2H), 7.59 (d, J=8.4 Hz, 3H), 7.54-7.45 (m, 2H), 7.43 (s, 1H), 7.25 (d, J=7.2 Hz, 1H), 1.32 (s, 9H). $^{13}$C NMR (75 MHz, DMSO-$d_6$) δ 179.41, 170.22, 161.42, 154.25, 144.10, 134.44, 131.73, 126.63, 126.17, 125.65, 124.03, 117.18, 116.11, 113.84, 101.39, 35.19, 31.32. HRMS (ESI) calcd for $C_{22}H_{20}ClN_4O_2$ 407.1275 (M+H)$^+$, found 407.1270.

N-(3-Chloro-5-(trifluoromethyl)phenyl)-2-(5-(4-(tert-butyl)phenyl)isoxazol-3-yl)-2-oxoacetohydrazonoyl cyanide (8). Compound 8 was prepared in 22% yield (two steps from 3a) by a procedure similar to that used to prepare compound 7. The title compound was obtained as a yellow solid. $^1$H NMR (300 MHz, DMSO-$d_6$) δ 7.88 (d, J=8.4 Hz, 2H), 7.78 (s, 2H), 7.62 (s, 1H), 7.58 (d, J=8.4 Hz, 2H), 7.42 (s, 1H), 1.32 (s, 9H). $^{13}$C NMR (75 MHz, DMSO-$d_6$) δ 179.13, 170.04, 166.63, 154.17, 135.45, 132.13 (q, J=33.7 Hz), 126.57, 126.09, 125.33, 124.10, 121.42, 121.16, 113.32, 101.48, 35.17, 31.32. HRMS (ESI) calcd for $C_{23}H_{19}F_3ClN_4O_2$ 475.1149 (M+H)$^+$, found 475.1145.

N-(3-Chloro-4-(trifluoromethyl)phenyl)-2-oxo-2-(5-(4-(tert-butyl)phenyl)isoxazol-3-yl)acetohydrazonoyl cyanide (9). Compound 9 was prepared in 28% yield (two steps from 3a) by a procedure similar to that used to prepare compound 7. The title compound was obtained as a yellow solid. $^1$H NMR (300 MHz, DMSO-$d_6$) δ 7.92-7.86 (m, 3H), 7.71 (s, 1H), 7.59 (m, 3H), 7.39 (s, 1H), 1.33 (s, 9H). $^{13}$C NMR (75 MHz, DMSO-$d_6$) δ 179.17, 169.93, 161.89, 154.15, 132.22, 129.66, 126.61, 126.13, 124.14, 119.99, 116.73, 115.06, 101.43, 35.18, 31.33. HRMS (ESI) calcd for $C_{23}H_{19}F_3ClN_4O_2$ 475.1149 (M+H)$^+$, found 475.1140.

N-(4-Chloro-3-(trifluoromethyl)phenyl)-2-oxo-2-(5-(4-(tert-butyl)phenyl)isoxazol-3-yl)acetohydrazonoyl cyanide (10). Compound 10 was prepared in 41% yield (two steps from 3a) by a procedure similar to that used to prepare compound 7. The title compound was obtained as a yellow solid. $^1$H NMR (300 MHz, DMSO-$d_6$) δ 8.00 (d, J=2.2 Hz, 1H), 7.88 (d, J=8.5 Hz, 2H), 7.75 (m, 2H), 7.59 (d, J=8.5 Hz, 2H), 7.41 (s, 1H), 1.33 (s, 9H). $^{13}$C NMR (75 MHz, DMSO-$d_6$) δ 179.21, 170.08, 161.68, 154.17, 133.34, 127.93 (q, J=31.0 Hz), 126.59, 126.09, 124.79, 124.07, 122.48, 116.81, 114.22, 101.33, 35.18, 31.33. HRMS (ESI) calcd for $C_{23}H_{19}F_3ClN_4O_2$ 475.1149 (M+H)$^+$, found 475.1147.

N-(3,5-Bis(trifluoromethyl)phenyl)-2-(5-(4-(tert-butyl)phenyl)isoxazol-3-yl)-2-oxoacetohydrazonoyl cyanide (11). Compound 11 was prepared in 26% yield (two steps from 3a) by a procedure similar to that used to prepare compound 7. The title compound was obtained as a yellow solid. $^1$H NMR (300 MHz, DMSO-d$_6$) δ 8.01 (s, 2H), 7.85 (d, J=8.2 Hz, 2H), 7.78 (s, 1H), 7.57 (d, J=8.4 Hz, 2H), 7.36 (s, 1H), 1.32 (s, 9H). $^{13}$C NMR (75 MHz, DMSO-d$_6$) δ 179.11, 169.61, 162.36, 153.99, 131.70 (dd, J=65.6, 32.8 Hz), 126.50, 125.97, 125.44, 124.22, 121.82, 118.67, 117.72, 114.15, 101.45, 35.14, 31.32. HRMS (ESI) calcd for C$_{24}$H$_{19}$F$_6$N$_4$O$_2$ 509.1412 (M+H)$^+$, found 519.1410.

N'-(3-Chloro-5-(trifluoromethyl)phenyl)-2-oxo-2-(5-phenylisoxazol-3 yl)acetohydrazonoyl cyanide (13). Compound 13 was prepared in 47% yield (two steps from 3b) by a procedure similar to that used to prepare compound 7. The title compound was obtained as a yellow solid. $^1$H NMR (300 MHz, DMSO-d$_6$) δ 7.96 (m, 2H), 7.78 (s, 2H), 7.63 (s, 1H), 7.58 (m, 3H), 7.51 (s, 1H). $^{13}$C NMR (75 MHz, DMSO-d$_6$) δ 179.11, 170.04, 161.55, 145.82, 135.49, 132.65 (q, J=32.7 Hz), 131.38, 129.80, 126.64, 126.23, 125.27, 121.65, 121.60, 120.93, 114.72, 113.00, 111.19, 102.05. HRMS (ESI) calcd for C$_{19}$H$_{11}$ClF$_3$N$_4$O$_2$ 419.0523 (M+H)$^+$, found 419.0516.

N-(3-Trifluromethyl-4-chlorophenyl)-2-oxo-2-(5-phenylisoxazol-3-yl)acetohydrazonoyl cyanide (14). Compound 14 was prepared in 43% yield (two steps from 3b) by a procedure similar to that used to prepare compound 7. The title compound was obtained as a yellow solid. $^1$H NMR (300 MHz, DMSO-d$_6$) δ 7.96 (d, J=7.5 Hz, 3H), 7.75 (d, J=3.0 Hz, 2H), 7.62-7.52 (m, 3H), 7.47 (s, 1H). $^{13}$C NMR (75 MHz, DMSO-d$_6$) δ 179.16, 169.93, 161.76, 143.47, 133.29, 131.33, 129.80, 127.93 (q, J=31.0 Hz), 126.69, 126.22, 124.78, 122.67, 121.16, 116.69, 114.16, 111.57, 101.88. HRMS (ESI) calcd for C$_{19}$H$_{11}$F$_3$ClN$_4$O$_2$ 419.0523 (M+H)$^+$, found 419.0536.

N-(3,5-Bis(trifluoromethyl)phenyl)-2-oxo-2-(5-phenylisoxazol-3-yl)acetohydrazonoyl cyanide (15). Compound 15 was prepared in 24% yield (two steps from ethyl 5-phenylisoxazole-3-carboxylate) by a procedure similar to that used to prepare compound 7. The title compound was obtained as a yellow solid. $^1$H NMR (300 MHz, DMSO-d$_6$) δ 8.03 (s, 2H), 7.93 (s, 2H), 7.81 (s, 1H), 7.56 (s, 3H), 7.48 (s, 1H). $^{13}$C NMR (75 MHz, DMSO-d$_6$) δ 179.09, 169.64, 166.63, 162.17, 131.74 (q, J=32.8 Hz), 131.24, 129.75, 126.78, 126.13, 125.39, 121.78, 118.42, 117.91, 114.41, 102.06. HRMS (ESI) calcd for C$_2$H$_{11}$F$_6$N$_4$O$_2$ 453.0786 (M+H)$^+$, found 453.0776.

N-(3-Chlorophenyl)-2-(5-(4-fluorophenyl)isoxazol-3-yl)-2-oxoacetohydrazonoyl cyanide (16). Compound 16 was prepared in 76% yield (two steps from 3c) by a procedure similar to that used to prepare compound 7. The title compound was obtained as a yellow solid. $^1$H NMR (300 MHz, DMSO-d$_6$) δ 8.10-8.02 (m, 2H), 7.57 (s, 1H), 7.52-7.39 (m, 5H), 7.26 (d, J=7.5 Hz, 1H). $^{13}$C NMR (75 MHz, DMSO-d$_6$) δ 179.29, 169.16, 163.89 (d, J=249.2 Hz), 161.57, 144.28, 134.43, 131.72, 128.97, 128.85, 125.66, 123.42, 117.16, 116.87, 116.23, 113.73, 111.11, 101.90. HRMS (ESI) calcd for C$_{18}$H$_{11}$FClN$_4$O$_2$ 369.0555 (M+H)$^+$, found 369.0549.

N-(3-Chloro-5-(trifluoromethyl)phenyl)-2-(5-(4-fluorophenyl)isoxazol-3-yl)-2-oxoacetohydrazonoyl cyanide (17). Compound 17 was prepared in 41% yield (two steps from 3c) by a procedure similar to that used to prepare compound 7. The title compound was obtained as a yellow solid. $^1$H NMR (300 MHz, DMSO-d$_6$) δ 8.04 (dd, J=8.6, 5.4 Hz, 2H), 7.76 (s, 2H), 7.61 (s, 1H), 7.49 (s, 1H), 7.43 (t, J=8.8 Hz, 2H). $^{13}$C NMR (75 MHz, DMSO-d$_6$) δ 179.04, 168.95, 163.85 (d, J=249.1 Hz) 161.89, 135.44, 132.10 (q, J=32.7 Hz), 128.87, 128.75, 125.32, 123.47, 121.45, 121.20, 117.11, 116.82, 114.45, 113.29, 111.64, 102.00. HRMS (ESI) calcd for C$_{19}$H$_{10}$F$_4$ClN$_4$O$_2$ 437.0428 (M+H)$^+$, found 437.0420.

N-(4-Chloro-3-(trifluoromethyl)phenyl)-2-(5-(4-fluorophenyl)isoxazol-3-yl)-2-oxoacetohydrazonoyl cyanide (18). Compound 18 was prepared in 66% yield (two steps from 3c) by a procedure similar to that used to prepare compound 7. The title compound was obtained as a yellow solid. $^1$H NMR (300 MHz, DMSO-d$_6$) δ 8.08-7.96 (m, 3H), 7.82-7.71 (m, 2H), 7.49 (s, 1H), 7.43 (t, J=8.8 Hz, 2H). $^{13}$C NMR (75 MHz, DMSO-d$_6$) δ 179.15, 169.17, 163.87 (d, J=247.5 Hz), 161.59, 142.56, 133.36, 128.90, 128.79, 126.75, 123.39, 122.34, 117.12, 116.82, 114.30, 111.13, 101.82. HRMS (ESI) calcd for C$_{19}$H$_{10}$F$_4$ClN$_4$O$_2$ 437.0428 (M+H)$^+$, found 437.0422.

N-(3-Chlorophenyl)-2-(5-(4-chlorophenyl)isoxazol-3-yl)-2-oxoacetohydrazonoyl cyanide (19). Compound 19 was prepared in 52% yield (two steps from 3d) by a procedure similar to that used to prepare compound 7. The title compound was obtained as a yellow solid. $^1$H NMR (300 MHz, DMSO-d$_6$) δ 7.99 (d, J=6.6 Hz, 2H), 7.57 (m, 6H), 7.25 (s, 1H). $^{13}$C NMR (75 MHz, DMSO-d$_6$) δ 179.17, 168.92, 161.62, 144.36, 136.04, 134.43, 131.69, 129.95, 128.10, 125.66, 125.50, 117.18, 116.28, 113.68, 111.15, 102.49. HRMS (ESI) calcd for C$_{18}$H$_{11}$Cl$_2$N$_4$O$_2$ 385.0259 (M+H)$^+$, found 385.0259.

N-(4-Chloro-3-(trifluoromethyl)phenyl)-2-oxo-2-(5-(4-chlorophenyl)isoxazol-3-yl)acetohydrazonoyl cyanide (20). Compound 20 was prepared in 81% yield (two steps from 3d) by a procedure similar to that used to prepare compound 7. The title compound was obtained as a yellow solid. $^1$H NMR (300 MHz, DMSO-d$_6$) δ 7.98 (d, J=8.1 Hz, 3H), 7.81-7.70 (m, 2H), 7.64 (d, J=8.4 Hz, 2H), 7.54 (s, 1H). $^{13}$C NMR (75 MHz, DMSO-d$_6$) δ 179.04, 170.79, 168.96, 161.59, 142.49, 136.02, 133.35, 129.92, 128.17, 128.05, 127.93 (q, J=31.0 Hz), 125.48, 122.29, 116.57, 114.28, 111.07, 102.44. HRMS (ESI) calcd for C$_{19}$H$_{10}$F$_3$Cl$_2$N$_4$O$_2$ 453.0133 (M+H)$^+$, found 453.0130.

N-(3,5-Bis(trifluoromethyl)phenyl)-2-(5-(4-chlorophenyl)isoxazol-3-yl)-2-oxoacetohydrazonoyl cyanide (21). Compound 21 was prepared in 38% yield (two steps from 3d) by a procedure similar to that used to prepare compound 7. The title compound was obtained as a yellow solid. $^1$H NMR (300 MHz, DMSO) δ 8.06 (s, 2H), 7.97 (d, J=8.3 Hz, 2H), 7.84 (s, 1H), 7.64 (d, J=8.2 Hz, 2H), 7.56 (s, 1H). $^{13}$C NMR (75 MHz, DMSO) δ 178.96, 168.60, 162.13, 135.91, 131.77 (q, J=33.1 Hz), 129.88, 127.96, 125.60, 125.37, 121.75, 118.25, 118.01, 102.63. HRMS (ESI) calcd for C$_{20}$H$_{10}$F$_6$ClN$_4$O$_2$ 487.0396 (M+H)$^+$, found 487.0390.

N-(3-Chlorophenyl)-2-(5-(4-methoxyphenyl)isoxazol-3-yl)-2-oxoacetohydrazonoyl cyanide (22). Compound 22 was prepared in 56% yield (two steps from 3e) by a procedure similar to that used to prepare compound 7. The title compound was obtained as a yellow solid. $^1$H NMR (300 MHz, DMSO) δ 7.91 (d, J=8.7 Hz, 2H), 7.57 (s, 1H), 7.52-7.42 (m, 2H), 7.33 (s, 1H), 7.25 (d, J=7.3 Hz, 1H), 7.12 (d, J=8.8 Hz, 2H), 3.85 (s, 3H). $^{13}$C NMR (75 MHz, DMSO) δ 179.46, 170.12, 161.67, 161.46, 134.43, 131.69, 128.06, 125.61, 119.33, 117.17, 116.25, 115.25, 113.75, 100.39, 55.92. HRMS (ESI) calcd for C$_{19}$H$_{14}$ClN$_4$O$_3$ 381.0754 (M+H)$^+$, found 381.0760.

N-(4-Chloro-3-(trifluoromethyl)phenyl)-2-oxo-2-(5-(4-methoxyphenyl)isoxazol-3-yl)acetohydrazonoyl cyanide (23). Compound 23 was prepared in 33% yield (two steps from 3e) by a procedure similar to that used to prepare compound 7. The title compound was obtained as a yellow solid. $^1$H NMR (300 MHz, DMSO) δ 8.00 (s, 1H), 7.90 (d, J=8.8 Hz, 2H), 7.81-7.70 (m, 2H), 7.34 (s, 1H), 7.12 (d, J=8.8 Hz, 2H), 3.85 (s, 3H). $^{13}$C NMR (75 MHz, DMSO) δ 179.35, 170.15, 161.65, 161.48, 133.35, 128.01, 126.66, 124.76, 122.34, 119.32, 116.70, 116.62, 115.22, 114.32, 100.31, 55.91. HRMS (ESI) calcd for $C_{20}H_{13}F_3ClN_4O_3$ 449.0628 (M+H)$^+$, found 381.0760.

N-(3,5-Bis(trifluoromethyl)phenyl)-2-(5-(4-chlorophenyl)isoxazol-3-yl)-2-oxoacetohydrazonoyl cyanide (24). Compound 24 was prepared in 14% yield (two steps from 3e) by a procedure similar to that used to prepare compound 7. The title compound was obtained as a yellow solid. $^1$H NMR (300 MHz, DMSO) δ 8.00 (s, 2H), 7.87 (d, J=8.4 Hz, 2H), 7.78 (s, 1H), 7.28 (s, 1H), 7.10 (d, J=8.5 Hz, 2H), 3.84 (s, 3H). $^{13}$C NMR (75 MHz, DMSO) δ 179.24, 169.56, 162.35, 161.51, 131.69 (q, J=32.9 Hz), 127.86, 125.44, 121.83, 119.55, 118.63, 117.74, 115.14, 114.16, 100.46, 55.89. HRMS (ESI) calcd for $C_{21}H_{13}F_6N_4O_3$ 483.0892 (M+H)$^+$, found 483.0890.

N-(3-Chlorophenyl)-2-(5-(furan-2-yl)isoxazol-3-yl)-2-oxoacetohydrazonoyl cyanide (25). To a solution of NaH (197 mg, 4.53 mmol) in anhydrous dioxane (3 mL) was added the solution of ethyl 5-(furan-2-yl)isoxazole-3-carboxylate 3f (350 mg, 1.81 mmol) in MeCN (3 mL) dropwise at 0° C. under nitrogen. The solution was stirred at 50° C. for 1 h, and then quenched with sat. NH$_4$Cl (2 mL) at 0° C. The mixture was poured onto ice/water (10 mL) and extracted with ethyl acetate (20 mL). The organic lay was dried over Na$_2$SO$_4$, filtered and concentrated under reduced pressure. The crude residue 4f (400 mg, quant.) was obtained as a yellow solid and directly used for next step without further purification.

Compound 25 was prepared in 40% yield (two steps from 3f) by a procedure similar to that used to prepare compound 7. The title compound was obtained as a yellow solid. $^1$H NMR (300 MHz, DMSO) δ 8.00 (s, 1H), 7.55 (s, 1H), 7.52-7.41 (m, 2H), 7.29 (d, J=3.5 Hz, 1H), 7.25 (d, J=6.7 Hz, 1H), 7.19 (s, 1H), 6.78 (dd, J=3.3, 1.7 Hz, 1H). $^{13}$C NMR (75 MHz, DMSO) δ 179.03, 161.57, 161.08, 146.46, 144.03, 141.98, 134.47, 131.72, 125.70, 117.12, 116.10, 113.80, 113.02, 112.68, 110.94, 100.98. HRMS (ESI) calcd for $C_{16}H_{10}ClN_4O_3$ 341.0441 (M+H)$^+$, found 341.0444.

N-(3-Chloro-5-(trifluoromethyl)phenyl)-2-(5-(furan-2-yl)isoxazol-3-yl)-2-oxoacetohydrazonoyl cyanide (26). Compound 26 was prepared in 38% yield (two steps from 3f) by a procedure similar to that used to prepare compound 25. The title compound was obtained as a yellow solid. $^1$H NMR (300 MHz, DMSO) δ 7.99 (d, J=1.7 Hz, 1H), 7.76 (s, 2H), 7.62 (s, 1H), 7.27 (d, J=3.5 Hz, 1H), 7.20 (s, 1H), 6.77 (dd, J=3.5, 1.8 Hz, 1H). $^{13}$C NMR (75 MHz, DMSO) δ 178.78, 161.50, 161.21, 146.42, 141.99, 135.52, 132.19 (d, J=32.9 Hz), 125.26, 121.65, 120.94, 114.68, 112.98, 112.56, 101.10. HRMS (ESI) calcd for $C_{17}H_9F_3ClN_4O_3$ 409.0315 (M+H)$^+$, found 409.0310.

N-(4-Chloro-3-(trifluoromethyl)phenyl)-2-(5-(furan-2-yl)isoxazol-3-yl)-2-oxoacetohydrazonoyl cyanide (27). Compound 27 was prepared in 36% yield (two steps from 3f) by a procedure similar to that used to prepare compound 25. The title compound was obtained as a yellow solid. $^1$H NMR (300 MHz, DMSO) δ 8.00 (d, J=1.7 Hz, 1H), 7.96 (d, J=2.1 Hz, 1H), 7.79 (d, J=8.7 Hz, 1H), 7.76-7.69 (m, 1H), 7.27 (d, J=3.6 Hz, 1H), 7.19 (s, 1H), 6.78 (dd, J=3.5, 1.8 Hz, 1H). $^{13}$C NMR (75 MHz, DMSO) δ 178.89, 161.52, 161.24, 146.41, 142.86, 142.01, 133.37, 128.00 (q, J=31.1 Hz), 126.73, 124.75, 122.44, 121.14, 116.65, 116.58, 114.30, 112.99, 112.58, 111.19, 100.96. HRMS (ESI) calcd for $C_{17}H_9F_3ClN_4O_3$ 409.0315 (M+H)$^+$, found 409.0312.

2-(Benzo[d]isoxazol-3-yl)-N-(3-chlorophenyl)-2-oxoacetohydrazonoyl cyanide (30). To a solution of CH$_3$CN (0.46 mL, 8.80 mmol) in anhydrous THF (8 mL) was added 1.6 M methyl lithium in diethyl ether (2.75 mL, 4.40 mmol) at −78° C. under nitrogen. The mixture was stirred at −78° C. for 0.5 h, and ethyl benzo[d]isoxazole-3-carboxylate 28 (0.42 g, 2.20 mmol) in THF (10 mL) was then added dropwise. The solution was stirred at −78° C. for 1 h and then quenched with acetic acid (0.26 mL, 4.40 mmol). The mixture was warmed to 0° C. and poured onto ice/water (10 mL) and extracted with ethyl acetate (20 mL). The organic lay was dried over Na$_2$SO$_4$, filtered and concentrated under reduced pressure. The crude residue 29 (400 mg, 98%) was obtained as a yellow solid and directly used for next step without further purification. $^1$H NMR (300 MHz, CDCl$_3$) δ 8.24 (d, J=8.0 Hz, 1H), 7.77-7.66 (m, 2H), 7.57-7.49 (m, 1H), 4.40 (s, 2H). $^{13}$C NMR (75 MHz, CDCl$_3$) δ 182.38, 164.73, 131.23, 126.16, 123.23, 118.36, 112.60, 110.18, 30.34.

Compound 30 was prepared in 53% yield (two steps from 28) by a procedure similar to that used to prepare compound 7. The title compound was obtained as a yellow solid. $^1$H NMR (300 MHz, DMSO-d$_6$) δ 8.05 (d, J=8.1 Hz, 1H), 7.94 (d, J=8.6 Hz, 1H), 7.77 (t, J=7.7 Hz, 1H), 7.51 (t, J=7.5 Hz, 1H), 7.44-7.33 (m, 3H), 7.26-7.19 (m, 1H). $^{13}$C NMR (75 MHz, DMSO-d$_6$) δ 179.64, 162.99, 155.16, 144.19, 134.42, 131.65, 131.50, 125.70, 125.65, 123.74, 120.52, 116.96, 116.15, 113.98, 111.13, 110.42. HRMS (ESI) calcd for $C_{16}H_{10}ClN_4O_2$ 325.0492 (M+H)$^+$, found 325.0483.

2-(Benzo[d]isoxazol-3-yl)-N-(3-chloro-5-(trifluoromethyl)phenyl)-2-oxoacetohydrazonoyl cyanide (31). Compound 31 was prepared in 33% yield (two steps from 28) by a procedure similar to that used to prepare compound 30. The title compound was obtained as a yellow solid. $^1$H NMR (300 MHz, DMSO-d$_6$) δ 8.04 (d, J=8.0 Hz, 1H), 7.94 (d, J=8.4 Hz, 1H), 7.76 (t, J=7.7 Hz, 1H), 7.60 (s, 3H), 7.49 (t, J=7.6 Hz, 1H). $^{13}$C NMR (75 MHz, DMSO-d$_6$) δ 179.40, 163.00, 155.37, 145.94, 135.46, 132.12 (q, J=32.8 Hz), 131.44, 125.63, 123.76, 121.59, 120.85, 120.56, 114.90, 112.83, 111.28, 110.39. HRMS (ESI) calcd for $C_{17}H_9F_3ClN_4O_2$ 393.0366 (M+H)$^+$, found 393.0376.

2-(Benzo[d]isoxazol-3-yl)-N-(3-chloro-4-(trifluoromethyl)phenyl)-2-oxoacetohydrazonoyl cyanide (32). Compound 32 was prepared in 22% yield (two steps from 28) by a procedure similar to that used to prepare compound 30. The title compound was obtained as a yellow solid. $^1$H NMR (300 MHz, DMSO-d$_6$) δ 8.02 (d, J=8.1 Hz, 1H), 7.93 (d, J=8.7 Hz, 1H), 7.84 (d, J=8.4 Hz, 1H), 7.76 (t, J=7.8 Hz, 1H), 7.56-7.42 (m, 3H). $^{13}$C NMR (75 MHz, DMSO-d$_6$) δ 179.41, 162.96, 132.27, 132.25, 131.44, 129.75, 129.68, 125.61, 123.72, 120.61, 119.55, 116.47, 115.39, 110.39. HRMS (ESI) calcd for $C_{17}H_9F_3ClN_4O_2$ 393.0366 (M+H)$^+$, found 393.0378.

2-(Benzo[d]isoxazol-3-yl)-N-(4-chloro-3-(trifluoromethyl)phenyl)-2-oxoacetohydrazonoyl cyanide (33). Compound 33 was prepared in 55% yield (two steps from 28) by a procedure similar to that used to prepare compound 30. The title compound was obtained as a yellow solid. $^1$H NMR (300 MHz, DMSO-d$_6$) δ 8.02 (d, J=8.0 Hz, 1H), 7.92 (d, J=8.5 Hz, 1H), 7.81-7.69 (m, 3H), 7.63 (dd, J=9.0, 2.2 Hz, 1H), 7.48 (t, J=7.5 Hz, 1H). $^{13}$C NMR (75 MHz, DMSO-d$_6$) δ 179.43, 163.01, 155.19, 142.68, 133.29, 131.43, 127.96 (q, J=31.2 Hz), 126.77, 125.61, 124.68, 123.66, 122.34, 121.06, 120.53, 116.45, 116.37, 114.51, 111.19, 110.36. HRMS (ESI) calcd for $C_{17}H_9F_3ClN_4O_2$ 393.0366 (M+H)$^+$, found 393.0374.

2-(Benzo[d]isoxazol-3-yl)-N-(3-chloro-5-fluorophenyl)-2-oxoacetohydrazonoyl cyanide (34). Compound 34 was prepared in 57% yield (two steps from 28) by a procedure similar to that used to prepare compound 30. The title compound was obtained as a yellow solid. $^1$H NMR (300 MHz, DMSO-$d_6$) δ 8.04 (d, J=7.9 Hz, 1H), 7.92 (d, J=8.5 Hz, 1H), 7.76 (t, J=7.7 Hz, 1H), 7.50 (t, J=7.5 Hz, 1H), 7.24-7.16 (m, 2H), 7.11 (d, J=10.3 Hz, 1H). $^{13}$C NMR (75 MHz, DMSO-$d_6$) δ 179.43, 162.99, 162.98 (d, J=245.0 Hz), 155.13, 146.02, 135.30 (d, J=5.9 Hz), 131.47, 125.66, 123.77, 120.54, 114.60, 113.59, 112.99, 112.65, 111.16, 110.43, 103.49 (d, J=26.6 Hz). HRMS (ESI) calcd for $C_{16}H_9FClN_4O_2$ 343.0398 (M+H)$^+$, found 343.0388.

2-(Benzo[d]isoxazol-3-yl)-N-(3-chloro-4-fluorophenyl)-2-oxoacetohydrazonoyl cyanide (35). Compound 35 was prepared in 44% yield (two steps from 28) by a procedure similar to that used to prepare compound 30. The title compound was obtained as a yellow solid. $^1$H NMR (300 MHz, DMSO-$d_6$) δ 8.04 (d, J=8.0 Hz, 1H), 7.92 (d, J=8.5 Hz, 1H), 7.80-7.72 (m, 1H), 7.54-7.36 (m, 4H). $^{13}$C NMR (75 MHz, DMSO-$d_6$) δ 179.48, 162.99, 155.29 (d, J=240.0 Hz), 155.07, 140.15, 131.46, 125.64, 123.70, 121.00, 120.74, 120.53, 118.95, 118.38, 118.08, 117.90, 117.80, 113.78, 111.15, 110.40. HRMS (ESI) calcd for $C_{16}H_9FClN_4O_2$ 343.0398 (M+H)$^+$, found 343.0387.

2-(Benzo[d]isoxazol-3-yl)-N-(3,5-bis(trifluoromethyl)phenyl)-2-oxoacetohydrazonoyl cyanide (36). Compound 36 was prepared in 31% yield (two steps from 28) by a procedure similar to that used to prepare compound 30. The title compound was obtained as a yellow solid. $^1$H NMR (300 MHz, DMSO-$d_6$) δ 8.02 (d, J=7.9 Hz, 1H), 7.93 (d, J=8.5 Hz, 1H), 7.88 (s, 2H), 7.81 (s, 1H), 7.75 (t, J=7.8 Hz, 1H), 7.47 (t, J=7.6 Hz, 1H). $^{13}$C NMR (75 MHz, DMSO-$d_6$) δ 179.35, 162.99, 155.56, 146.13, 132.83 (q, J=32.9 Hz), 131.37, 125.55, 125.24, 123.70, 121.62, 120.59, 117.75, 115.06, 111.39, 110.34. HRMS (ESI) calcd for $C_{18}H_9F_6N_4O_2$ 427.0630 (M+H)$^+$, found 427.0617.

2-(Benzo[d]isoxazol-3-yl)-N-(3,4,5-trifluorophenyl)-2-oxoacetohydrazonoyl cyanide (37). Compound 37 was prepared in 25% yield (two steps from 28) by a procedure similar to that used to prepare compound 30. The title compound was obtained as a brown solid. $^1$H NMR (300 MHz, DMSO-$d_6$) δ 8.02 (d, J=7.7 Hz, 1H), 7.91 (d, J=8.6 Hz, 1H), 7.76 (t, J=7.7 Hz, 1H), 7.50 (t, J=7.5 Hz, 1H), 7.17 (dd, J=9.1, 6.8 Hz, 2H). $^{13}$C NMR (75 MHz, DMSO-$d_6$) δ 179.20, 170.81, 162.92, 155.28, 151.14 (ddd, J=246.5, 10.5, 5.0 Hz), 140.66, 138.18, 135.11, 131.39, 125.58, 123.71, 120.64, 114.17, 111.60, 110.41, 102.22 (d, J=24.6 Hz). HRMS (ESI) calcd for $C_{16}H_8F_3N_4O_2$ 345.0599 (M+H)$^+$, found 345.0590.

2. In Vitro Guanine Nucleotide Exchange Factor (GEF) Activity Assay of EPAC Proteins In vitro EPAC GEF activity was acquired as previously described (Zhu et al., Sci. Rep. (2015) 5:9344). Briefly, the assay was performed using 500 nM Rap1b-BODIPY-GDP and 200 nM EPAC proteins in buffer containing 50 mM Tris-HCl pH 7.5, 50 mM NaCl, 5 mM MgCl$_2$, 1 mM DTT, 50 mM GDP and the indicated concentrations of test compounds at room temperature using half-area 96-well plates (Corning Costar 3915). The exchange reaction was monitored using a Spectramax M2 Plate Reader (Molecular Devices) with the excitation/emission wavelengths set at 485/515 nm. The reaction rate constant ($k_{obs}$) was determined by globally fitting the experimental data to a single exponential equation. Quantification was processed by nominalizing the observed $k_{obs}$ in the presence of inhibitor with the rate constant in the presence of 20 μM cAMP (no inhibitor) ($k_{cAmp}$) and the rate constant without cAMP or inhibitor ($k_0$) using equation: Relative GEF activity=($k_{obs}$−$k_0$)/($k_{cAmp}$−$k_0$)×100.

3. Molecular Docking Studies

The docking study was performed with Schrödinger Small-Molecule Drug Discovery Suite (Small-Molecule Drug Discovery Suite 2016-4, Schrödinger, LLC, New York, N.Y., 2016). The crystal structure of EPAC$_2$ (PDB code: 3CF6) was downloaded from RCSB PDB Bank and prepared with Protein Prepared Wizard (Schrödinger Release 2016-4: Schrödinger Suite 2016-4 Protein Preparation Wizard, Schrödinger, LLC, New York, N.Y., 2016). During this step, hydrogens were added, crystal waters were removed, and partial charges were assigned using the OPLS-2005 force field. The 3D structures of ESI-09, NY0617 and NY0562 were created with Schrödinger Maestro (Schrödinger Release 2016-4: Maestro, Schrödinger, LLC, New York, N.Y., 2016) and the initial lowest energy conformations were calculated with LigPrep (Schrödinger Release 2016-4: LigPrep, Schrödinger, LLC, New York, N.Y., 2016). For all dockings, the grid center was chosen on the centroid of included ligand of PDB structure CBD-B site and a 24×24×24 Å grid box size was used. All dockings were employed with Glide (Schrödinger Release 2016-4: Glide, Schrödinger, LLC, New York, N.Y., 2016) using the XP protocol. Docking poses were incorporated into Schrödinger Maestro for a visualization of ligand-receptor interactions and overlay analysis.

EXAMPLE 2

Figure 5:
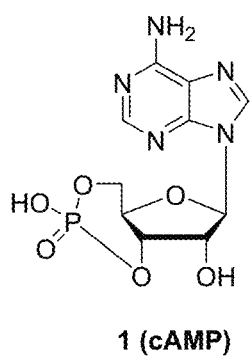
FIG. 5. The structures of cAMP and representative EPAC antagonists.
Figure 5:
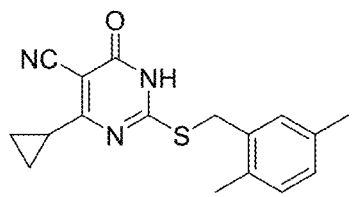
Figure 5:
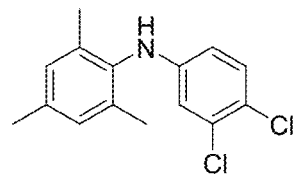
Figure 5:
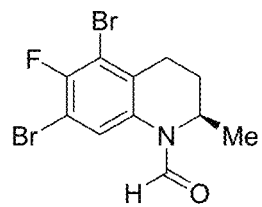
Figure 5:
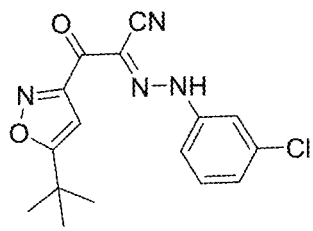
Figure 5:
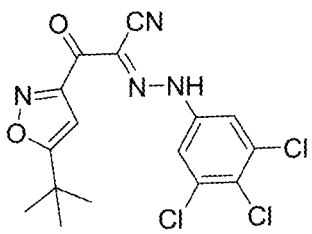
Figure 6A:
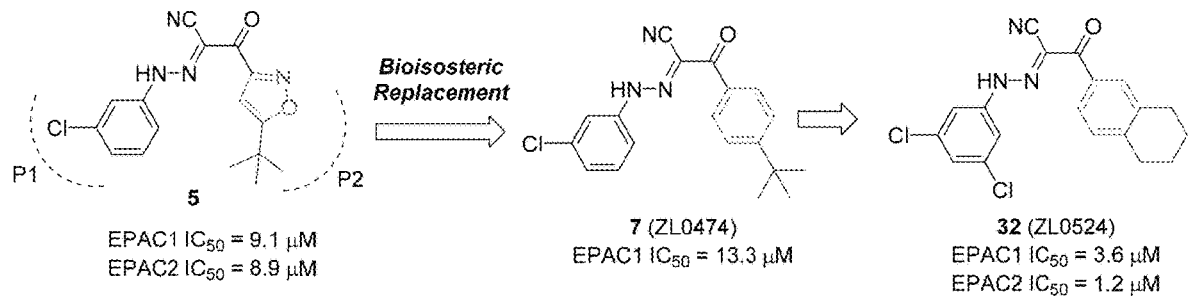
FIGS. 6A-6C.
Figure 6B:
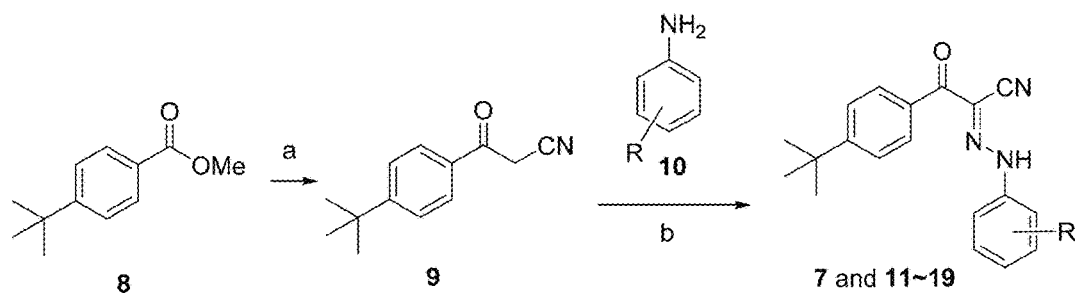
Figure 6C:
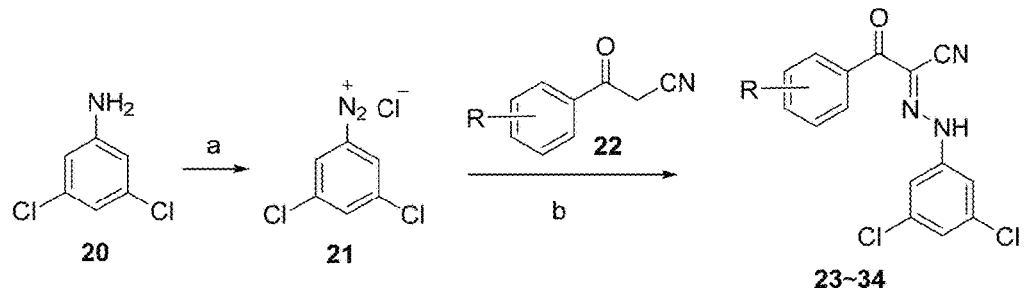

Given the physiological and pathophysiological significance of EPAC proteins, developing pharmacological EPAC modulators has attracted more and more attention. Most EPAC agonists are derivatives of cAMP, while non-cyclic nucleotide ligands usually display EPAC inhibitory activities. Cheng group developed a sensitive and robust fluorescence-based high throughput (HTS) assay, (Tsalkova et al., PloS one, (2012) 7:e30441) and discovered a series of non-cyclic nucleotide EPAC inhibitors (Tsalkova et al., Proc. Natl. Acad. Sci. U.S.A., (2012) 109:18613-18). After extensive modifications by the inventors, dihydropyrimidine 2 (HJC0198, FIG. 5) was obtained with IC$_{50}$ value of 4.0 μM against EPAC2. It selectively blocked cAMP-induced EPAC activation without affecting cAMP-mediated PKA activation at the concentration of 25 μM. Diphenylamine 3 (MAY0132), displayed potent and selective EPAC2 inhibitory activity with IC$_{50}$ value of 0.4 μM, while it had no significant inhibition against EPAC1 at 100 μM.

A. General Procedure for Preparation of Compounds

Scheme 3 (FIG. 5B). Synthesis of compounds 7 and 11~20 is illustrated in FIG. 5B. Scheme 2. Synthesis of compounds 24~34 is illustrated in FIG. 5C. Compound numbers are specific to each example in which they occur. To a solution of anilines (0.25 mmol) in 1 mL H$_2$O and 1 mL CH$_3$CN, 10% HCl (1.0 mmol) was added at 0° C. After stirring at rt. for 30 min, NaNO$_2$ (0.3 mmol) in 1 mL H$_2$O was added. After stirring at ° C. for 5 min, NaOAc (1.5 mmol) and 3-(substitutedphenyl)-3-oxopropanenitrile (0.25 mmol) in 2 mL EtOH were added. The mixture was extracted with DCM and purified by silica gel column (PE/EA=20/1–5/1) to give the desired product.

(E)-2-(4-(tert-butyl)phenyl)-N-(3-chlorophenyl)-2-oxoacetohydrazonoyl cyanide (7, ZL0474). Yellow solid, 84%. $^1$H NMR (300 MHz, DMSO-d$_6$) δ 12.38 (s, 1H), 7.85 (d, J=8.2 Hz, 2H), 7.57 (d, J=8.2 Hz, 2H), 7.46-7.32 (m, 3H), 7.19 (d, J=7.4 Hz, 1H), 1.33 (s, 9H). $^{13}$C NMR (75 MHz, DMSO-d$_6$) δ 187.16, 156.09, 144.01, 134.38, 133.82, 131.69, 130.36, 125.33, 124.82, 116.51, 115.40, 114.71, 111.69, 35.29, 31.31. HR ESI-MS (M+Na)$^+$ m/z=362.0126 (calcd for C$_{19}$H$_{18}$ClN$_3$NaO:362.1036).

(E)-2-(4-(tert-butyl)phenyl)-N-(3,5-dichlorophenyl)-2-oxoacetohydrazonoyl cyanide (11, ZL0475). Yellow solid, 69%. $^1$H NMR (300 MHz, DMSO-d$_6$) δ 12.43 (s, 1H), 7.81 (d, J=8.0 Hz, 2H), 7.56 (d, J=8.0 Hz, 2H), 7.31 (s, 2H), 1.33 (s, 9H). $^{13}$C NMR (75 MHz, DMSO-d$_6$) δ 187.29, 166.62, 156.14, 145.04, 135.30, 133.76, 130.36, 125.25, 123.96, 115.50, 115.30, 111.49, 35.28, 31.29. HR ESI-MS (M+Na)$^+$ m/z=396.0670 (calcd for C$_{19}$H$_{17}$Cl$_2$N$_3$NaO:396.0646).

(E)-2-(4-(tert-butyl)phenyl)-N-(3-chloro-4-fluorophenyl)-2-oxoacetohydrazonoyl cyanide (12, ZL0476). Yellow solid, quant. $^1$H NMR (300 MHz, MeOD) δ 7.89 (d, J=8.5 Hz, 2H), 7.58 (d, J=8.5 Hz, 2H), 7.45 (dd, J=6.4, 2.5 Hz, 1H), 7.36-7.22 (m, 2H), 1.39 (s, 9H). $^{13}$C NMR (75 MHz, MeOD) δ 187.18, 156.84, 156.39, 153.59, 139.18, 139.14, 133.33, 129.81, 124.79, 121.51, 121.25, 117.85, 117.26, 116.96, 115.89, 115.80, 114.70, 109.94, 34.60, 30.11. HR ESI-MS (M+Na)$^+$ m/z=380.0933 (calcd for C$_{19}$H$_{17}$ClFN$_3$NaO:380.0942).

(E)-2-(4-(tert-butyl)phenyl)-N-(3-chloro-5-fluorophenyl)-2-oxoacetohydrazonoyl cyanide (13, ZL0477). Yellow solid, quant. $^1$H NMR (300 MHz, MeOD) δ 7.88 (d, J=8.4 Hz, 2H), 7.59 (d, J=8.4 Hz, 2H), 7.21 (s, 1H), 7.04 (d, J=10.2 Hz, 1H), 6.94 (d, J=8.4 Hz, 1H), 1.39 (s, 9H). $^{13}$C NMR (75 MHz, MeOD) δ 187.07, 164.99, 161.71, 156.55, 144.61, 135.93, 135.77, 133.19, 129.84, 124.80, 112.00, 111.96, 111.60, 111.26, 109.70, 101.86, 101.50, 34.61, 30.09. HR ESI-MS (M+H)$^+$ m/z=358.1123 (calcd for C$_{19}$H$_{18}$ClFN$_3$O: 358.1122).

(E)-2-(4-(tert-butyl)phenyl)-2-oxo-N-(3,4,5-trifluorophenyl)acetohydrazonoyl cyanide (14, ZL0478). Yellow solid, 74%. $^1$H NMR (300 MHz, DMSO-d$_6$) δ 12.39 (s, 1H), 7.84 (d, J=8.1 Hz, 2H), 7.57 (d, J=8.1 Hz, 2H), 7.25-7.04 (m, 2H), 1.32 (s, 9H). $^{13}$C NMR (75 MHz, DMSO-d$_6$) δ 186.87, 156.30, 152.90, 152.83, 152.76, 152.69, 149.64, 149.57, 149.50, 149.43, 139.08, 133.59, 130.35, 125.40, 115.56, 111.57, 101.53, 101.20, 35.30, 31.28. HR ESI-MS (M+Na)$^+$ m/z=382.1158 (calcd for C$_{19}$H$_{16}$F$_3$N$_3$NaO:382.1143).

(E)-N-(3,5-bis(trifluoromethyl)phenyl)-2-(4-(tert-butyl)phenyl)-2-oxoacetohydrazonoyl cyanide (15, ZL0479). Yellow solid, 67%. $^1$H NMR (300 MHz, MeOD) δ 7.88 (m, 4H), 7.69 (s, 1H), 7.62-7.56 (m, 2H), 1.40 (s, 9H). $^{13}$C NMR (75 MHz, MeOD) δ 187.29, 156.50, 144.04, 133.30, 133.18, 132.86, 132.41, 131.97, 129.82, 128.53, 124.92, 124.70, 121.32, 117.71, 116.96, 116.90, 116.85, 116.80, 116.75, 116.23, 115.80, 115.76, 109.47, 34.57, 30.05. HR ESI-MS (M+H)$^+$ m/z=442.1355 (calcd for C$_{21}$H$_{18}$F$_6$N$_3$O:442.1354).

(E)-2-(4-(tert-butyl)phenyl)-N-(4-chloro-3-(trifluoromethyl)phenyl)-2-oxoacetohydrazonoyl cyanide (16, ZL0559). Yellow solid, 73%. $^1$H NMR (300 MHz, DMSO-d$_6$) δ 12.57 (s, 1H), 7.84 (d, J=8.3 Hz, 2H), 7.78 (d, J=2.1 Hz, 1H), 7.73 (d, J=8.8 Hz, 1H), 7.62 (dd, J=8.8, 2.0 Hz, 1H), 7.54 (d, J=8.4 Hz, 2H), 1.32 (s, 9H). $^{13}$C NMR (75 MHz, DMSO-d$_6$) δ 187.17, 156.11, 142.01, 133.68, 133.31, 130.37, 128.14, 127.73, 125.86, 125.63, 121.58, 115.78, 115.71, 115.63, 115.55, 115.30, 111.53, 35.25, 31.25. HR ESI-MS (M+Na)$^+$ m/z=430.0957 (calcd for C$_{2}$H$_{17}$F$_3$N$_3$ClNaO:430.0910).

(E)-2-(4-(tert-butyl)phenyl)-N-(3-chloro-5-(trifluoromethyl)phenyl)-2-oxoacetohydrazonoyl cyanide (17, ZL0560). Yellow solid, 76%. $^1$H NMR (300 MHz, DMSO-d$_6$) δ 12.58 (s, 1H), 7.81 (d, J=7.7 Hz, 2H), 7.56 (m, 5H), 1.32 (s, 9H). $^{13}$C NMR (75 MHz, DMSO-d$_6$) δ 187.37, 156.13, 144.79, 135.46, 133.68, 132.39, 131.95, 130.36, 125.16, 120.80, 120.00, 115.71, 111.78, 111.33, 35.23, 31.22. HR ESI-MS (M+Na)$^+$ m/z=430.0956 (calcd for C$_{20}$H$_{17}$F$_3$N$_3$ClNaO:430.0910).

(E)-2-(4-(tert-butyl)phenyl)-N-(3-chloro-4-(trifluoromethyl)phenyl)-2-oxoacetohydrazonoyl cyanide (18, ZL0561). Yellow solid, 79%. $^1$H NMR (300 MHz, DMSO-d$_6$) δ 12.55 (s, 1H), 7.86 (d, J=8.3 Hz, 3H), 7.57 (d, J=8.6 Hz, 3H), 7.45 (d, J=8.7 Hz, 1H), 1.33 (s, 9H). $^{13}$C NMR (75 MHz, DMSO-d$_6$) δ 186.91, 156.38, 146.94, 133.47, 132.30, 130.48, 129.95, 129.89, 129.82, 129.75, 125.41, 122.68, 122.27, 121.85, 121.61, 121.44, 118.85, 116.54, 115.08, 111.38, 35.31, 31.28. HR ESI-MS (M+H)$^+$ m/z=408.1061 (calcd for C$_{20}$H$_{18}$F$_3$N$_3$ClO:408.1090).

(E)-2-(4-(tert-butyl)phenyl)-2-oxo-N-(3,4,5-trichlorophenyl)acetohydrazonoyl cyanide (19, ZL0562). Yellow solid, 89%. $^1$H NMR (300 MHz, DMSO-d$_6$) δ 7.81 (d, J=8.3 Hz, 2H), 7.55 (d, J=8.3 Hz, 2H), 7.46 (s, 2H), 1.32 (s, 9H). $^{13}$C NMR (75 MHz, DMSO-d$_6$) δ 187.16, 156.21, 142.62, 134.08, 133.65, 130.37, 125.26, 125.15, 117.00, 115.82, 111.44, 35.28, 31.28. HR ESI-MS (M+Na)$^+$ m/z=430.0265 (calcd for C$_{19}$H$_{16}$N$_3$Cl$_3$NaO:430.0257).

(E)-2-(4-chlorophenyl)-N-(3,5-dichlorophenyl)-2-oxoacetohydrazonoyl cyanide (23, ZL0491). Yellow solid, 81%. $^1$H NMR (300 MHz, DMSO-d$_6$) δ 7.86 (d, J=8.5 Hz, 2H), 7.59 (d, J=8.5 Hz, 2H), 7.29 (m, 3H). $^{13}$C NMR (75 MHz, DMSO-d$_6$) δ 186.51, 147.25, 137.33, 136.10, 135.21, 132.13, 128.45, 123.86, 115.97, 114.81, 112.44. HR ESI-MS (M+H)$^+$ m/z=351.9812 (calcd for C$_{15}$H$_9$N$_3$Cl$_3$O:351.9811).

(E)-2-(3-chlorophenyl)-N-(3,5-dichlorophenyl)-2-oxoacetohydrazonoyl cyanide (24, ZL0546). Yellow solid (78%). $^1$H NMR (300 MHz, DMSO) δ 12.50 (s, 1H), 7.96 (s, 1H), 7.75 (m, 2H), 7.57 (t, J=7.8 Hz, 1H), 7.33 (m, 3H). $^{13}$C NMR (75 MHz, DMSO-d$_6$) δ 186.30, 144.89, 138.25, 135.38, 133.20, 132.59, 130.56, 130.36, 128.71, 124.27, 115.40, 111.28. HR ESI-MS (M+H)$^+$ m/z=351.9812 (calcd for C$_{15}$H$_9$N$_3$Cl$_3$O:351.9815).

(E)-N-(3,5-dichlorophenyl)-2-oxo-2-(4-(trifluoromethoxy)phenyl)acetohydrazonoyl cyanide (25, ZL0564). Yellow solid, 94%. $^1$H NMR (300 MHz, DMSO-d$_6$) δ 12.52 (s, 1H), 7.98 (d, J=8.5 Hz, 2H), 7.52 (d, J=8.3 Hz, 2H), 7.31 (s, 1H), 7.27 (s, 2H). $^{13}$C NMR (75 MHz, DMSO-d$_6$) δ 186.61, 151.37, 144.91, 135.54, 135.30, 132.65, 124.17, 120.63, 115.36, 111.35. HR ESI-MS (M+H)$^+$ m/z=402.0032 (calcd for C$_{16}$H$_9$N$_3$Cl$_2$O$_2$F$_3$:402.0024).

Methyl (E)-4-(2-cyano-2-(2-(3,5-dichlorophenyl)hydrazono)acetyl)benzoate (26, ZL0566). Yellow solid, quant. $^1$H NMR (300 MHz, DMSO-d$_6$) δ 12.53 (s, 1H), 8.06 (d, J=8.0 Hz, 2H), 7.94 (d, J=8.1 Hz, 2H), 7.29 (s, 1H), 7.26 (s, 2H), 3.90 (s, 3H). $^{13}$C NMR (75 MHz, DMSO-d$_6$) δ 187.21, 166.12, 146.52, 141.22, 135.22, 132.66, 130.47, 129.02, 124.05, 115.85, 115.05, 112.07, 52.93. HR ESI-MS (M+Na)$^+$ m/z=398.0081 (calcd for C$_{17}$H$_{11}$N$_3$Cl$_2$NaO$_3$: 398.0075).

(E)-2-([1,1'-biphenyl]-4-yl)-N-(3,5-dichlorophenyl)-2-oxoacetohydrazonoyl cyanide (27, ZL0536). Yellow solid, quant. $^1$H NMR (300 MHz, DMSO-d$_6$) δ 7.98 (d, J=8.3 Hz, 2H), 7.85 (d, J=8.4 Hz, 2H), 7.76 (d, J=7.3 Hz, 2H), 7.53 (t, J=7.4 Hz, 2H), 7.44 (t, J=7.3 Hz, 1H), 7.35 (s, 3H). $^{13}$C NMR (75 MHz, DMSO-d$_6$) δ 187.14, 144.49, 139.40, 135.33, 131.19, 129.63, 128.87, 127.46, 126.67, 124.02, 115.44, 111.70. HR ESI-MS (M+H)+ m/z=394.0490 (calcd for $C_{21}H_{14}N_3Cl_2O$:394.0514).

(E)-N-(3,5-dichlorophenyl)-2-(3,4-dimethoxyphenyl)-2-oxoacetohydrazonoyl cyanide (28, ZL0631). Yellow solid, 97%. $^1$H NMR (300 MHz, DMSO-$d_6$) δ 12.32 (s, 1H), 7.59 (d, J=6.9 Hz, 2H), 7.38 (s, 2H), 7.32 (s, 1H), 7.11 (d, J=8.8 Hz, 1H), 3.87 (s, 3H), 3.82 (s, 3H). $^{13}$C NMR (75 MHz, DMSO-$d_6$) δ 185.33, 153.44, 148.45, 145.07, 135.33, 128.41, 124.97, 123.84, 115.88, 115.14, 113.64, 111.62, 111.28, 56.25, 56.00. HR ESI-MS (M+H)+ m/z=378.0416 (calcd for $C_{17}H_{14}N_3Cl_2O_3$:378.0412).

(E)-N-(3,5-dichlorophenyl)-2-oxo-2-(4-(piperidin-1-ylmethyl)phenyl)acetohydrazonoyl cyanide (29, ZL0644). Yellow solid, 72%. $^1$H NMR (300 MHz, DMSO-$d_6$) δ 7.77 (d, J=7.8 Hz, 2H), 7.53 (d, J=7.8 Hz, 2H), 7.14 (s, 2H), 7.10 (s, 1H), 4.32 (s, 2H), 3.33 (s, 2H), 2.95 (s, 2H), 1.72 (m, 6H). $^{13}$C NMR (75 MHz, DMSO-$d_6$) δ 187.15, 156.79, 142.23, 134.64, 130.49, 130.00, 122.48, 118.35, 116.67, 112.06, 59.48, 52.44, 23.01, 21.83. HR ESI-MS (M+H)±m/z=415.1085 (calcd for $C_{21}H_{21}N_4Cl_2O$:415.1092).

(E)-N-(3,5-dichlorophenyl)-2-(4-(morpholinomethyl)phenyl)-2-oxoacetohydrazonoyl cyanide (30, ZL0668). Yellow solid, quant. $^1$H NMR (300 MHz, DMSO-$d_6$) δ 7.82 (d, J=7.9 Hz, 2H), 7.52 (d, J=7.9 Hz, 2H), 7.20 (d, J=4.6 Hz, 3H), 4.10 (s, 2H), 3.72 (s, 4H), 2.91 (s, 4H). $^{13}$C NMR (75 MHz, DMSO-$d_6$) δ 191.98, 144.34, 139.65, 134.93, 134.63, 127.81, 121.93, 119.44, 118.18, 69.67, 65.47, 57.06. HR ESI-MS (M+H)+ m/z=417.0887 (calcd for $C_{20}H_{19}N_4Cl_2O_2$: 417.0885).

(E)-2-(4-cyclohexylphenyl)-N-(3,5-dichlorophenyl)-2-oxoacetohydrazonoyl cyanide (31, ZL0634). Yellow solid, 82%. $^1$H NMR (300 MHz, DMSO-$d_6$) δ 12.42 (s, 1H), 7.80 (d, J=5.8 Hz, 2H), 7.52-7.20 (m, 5H), 2.59 (s, 1H), 1.78 (m, 5H), 1.31 (m, 5H). $^{13}$C NMR (75 MHz, DMSO-$d_6$) δ 187.07, 153.17, 144.97, 135.30, 134.03, 130.63, 126.79, 123.95, 115.58, 115.25, 111.48, 44.22, 34.04, 26.65, 25.94. HR ESI-MS (M+H)+ m/z=400.1030 (calcd for $C_{21}H_{20}N_3Cl_2O$:400.0983).

(E)-N-(3,5-dichlorophenyl)-2-oxo-2-(5,6,7,8-tetrahydronaphthalen-2-yl)acetohydrazonoyl cyanide (32, ZL0524). Yellow solid, 59%. $^1$H NMR (300 MHz, DMSO-$d_6$) δ 12.42 (s, 1H), 7.68 (s, 1H), 7.58 (d, J=8.0 Hz, 1H), 7.34 (s, 3H), 7.21 (d, J=8.0 Hz, 1H), 2.81 (s, 4H), 1.78 (s, 4H). $^{13}$C NMR (75 MHz, DMSO-$d_6$) δ 186.93, 144.98, 142.79, 136.83, 135.34, 133.44, 131.65, 129.19, 127.36, 123.94, 115.57, 115.23, 111.44, 29.39, 29.28, 22.95, 22.84. HR ESI-MS (M+H)+ m/z=372.0667 (calcd for $C_{19}H_{16}N_3Cl_2O$: 372.0670).

(E)-N-(3,5-dichlorophenyl)-2-(naphthalen-2-yl)-2-oxoacetohydrazonoyl cyanide (33, ZL0682). Yellow solid, 82%. $^1$H NMR (300 MHz, DMSO-$d_6$) δ 12.50 (s, 1H), 8.62 (s, 1H), 8.13-7.99 (m, 3H), 7.91 (d, J=8.5 Hz, 1H), 7.73-7.59 (m, 2H), 7.36 (s, 2H), 7.31 (s, 1H). $^{13}$C NMR (75 MHz, DMSO-$d_6$) δ 187.15, 144.92, 135.31, 135.14, 133.43, 132.25, 129.69, 129.09, 128.16, 128.04, 127.47, 126.11, 124.06, 115.69, 115.36, 111.46. HR ESI-MS (M+H)+ m/z=369.0299 (calcd for $C_{19}H_{12}N_3Cl_2O$:369.0310).

(E)-N-(3,5-dichlorophenyl)-2-oxo-2-(quinolin-6-yl)acetohydrazonoyl cyanide (34, ZL0642). Yellow solid, 37%. $^1$H NMR (300 MHz, DMSO-$d_6$) δ 9.04 (s, 1H), 8.67 (d, J=21.2 Hz, 1H), 8.55 (d, J=8.1 Hz, 1H), 8.15 (m, 2H), 7.66 (dd, J=8.1, 4.3 Hz, 1H), 7.31 (s, 3H). $^{13}$C NMR (75 MHz, DMSO-$d_6$) δ 189.73, 187.00, 153.87, 153.18, 150.10, 149.24, 145.38, 138.32, 137.96, 135.27, 134.29, 132.74, 132.23, 131.62, 130.06, 130.00, 128.88, 127.63, 127.54, 127.36, 124.09, 123.13, 122.88, 116.29, 115.57, 115.34, 111.65. HR ESI-MS (M+Na)+ m/z=390.0174 (calcd for $C_{18}H_{10}N_4Cl_2NaO$:390.0177).

B. Biological Activity

TABLE 4

IC50 values of substituted 2-(4-(tert-butyl)phenyl)-N-phenyl-2-oxoacetohydrazonoyl cyanides for inhibiting EPAC1/2 GEF activity.

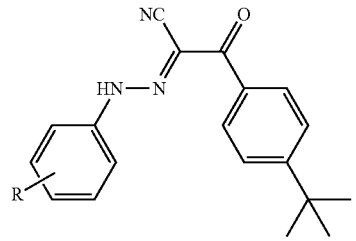

| Entry | Code | R | Rap 1b-bGDP Epac1 $IC_{50}$ (μM) | Rap 1b-bGDP Epac2 $IC_{50}$ (μM) |
|---|---|---|---|---|
| 5 | ESI-09 | — | 10.8 ± 1.6 | 4.4 ± 0.5 |
| 7 | ZL0474 | 3-Cl | 13.3 ± 3.0 | 28.4 ± 5.6 |
| 11 | ZL0475 | 3,5-di Cl | 5.4 ± 0.7 | 2.5 ± 0.6 |
| 12 | ZL0476 | 3-Cl, 4-F | 12.4 ± 0.9 | ND |
| 13 | ZL0477 | 3-Cl, 5-F | 6.4 ± 1.4 | 3.4 ± 0.6 |
| 14 | ZL0478 | 3,4,5-tri F | 24.4 ± 5.7 | 15.8 ± 3.8 |
| 15 | ZL0479 | 3,5-di $CF_3$ | 5.5 ± 0.7 | 6.3 ± 0.9 |
| 16 | ZL0559 | 3-$CF_3$, 4-Cl | 6.1 ± 1.0 | 12.4 ± 3.9 |
| 17 | ZL0560 | 3-Cl, 5-$CF_3$ | 5.6 ± 0.9 | 5.4 ± 1.1 |
| 18 | ZL0561 | 3-Cl, 4-CF3 | 50.8 ± 14.6 | ND |
| 19 | ZL0562 | 3,4,5-tri Cl | 13.9 ± 3.6 | 3.0 ± 0.4 |

[a]ND: not determined.

TABLE 5

$IC_{50}$ values of substituted 2-phenyl-N-(3,5-dichlorophenyl)-2-oxoacetohydrazonoyl cyanides for inhibiting EPAC1/2 GEF activity.

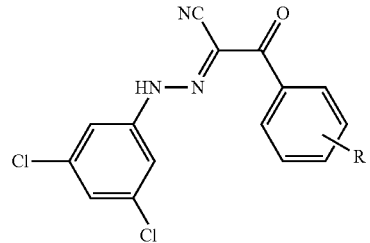

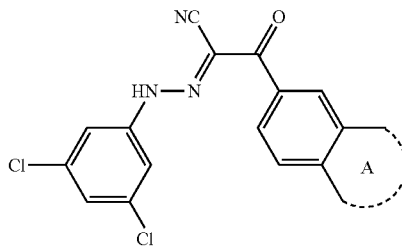

| Entry | NO | R or A | Rap 1b-bGDP Epac1 $IC_{50}$ (μM) | Rap 1b-bGDP Epac2 $IC_{50}$ (μM) |
|---|---|---|---|---|
| 23 | ZL0491 | 4-Cl | >300 | ND[a] |
| 24 | ZL0546 | 3-Cl | >300 | ND |

TABLE 5-continued

IC$_{50}$ values of substituted 2-phenyl-N-(3,5-dichlorophenyl)-2-oxoacetohydrazonoyl cyanides for inhibiting EPAC1/2 GEF activity.

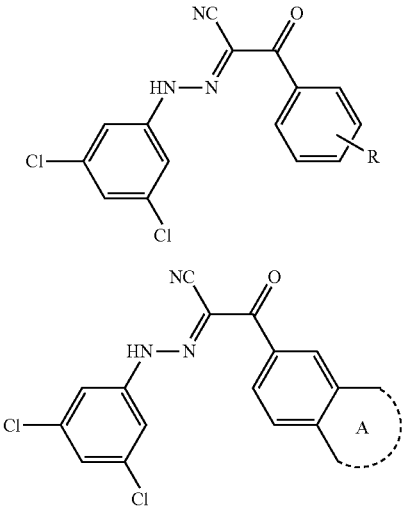

| Entry | NO | R or A | Rap 1b-bGDP Epac1 IC$_{50}$ (μM) | Rap 1b-bGDP Epac2 IC$_{50}$ (μM) |
|---|---|---|---|---|
| 25 | ZL0564 | 4-OCF$_3$ | 40.9 ± 6.8 | ND |
| 26 | ZL0566 | 4-CO$_2$Me | 29.3 ± 6.2 | ND |
| 27 | ZL0536 | 4-Ph | >300 | ND |
| 28 | ZL0631 | 3,4-di OMe | >300 | ND |
| 29 | ZL0644 | 4-Piperidin-1-ylmethyl | 39.4 ± 4.7 | ND |
| 30 | ZL0668 | 4-Morpholinomethyl | 14.6 ± 5.7 | ND |
| 31 | ZL0634 | 4-Cyclohexane | 32.4 ± 9.5 | ND |
| 32 | ZL0524 | cyclohexyl | 3.6 ± 0.3 | 1.2 ± 0.1 |
| 33 | ZL0682 | phenyl | 11.3 ± 1.4 | 2.5 ± 0.5 |
| 34 | ZL0642 | pyridyl | 19.6 ± 6.7 | ND |

$^a$ND: not determined.

Figure 7:
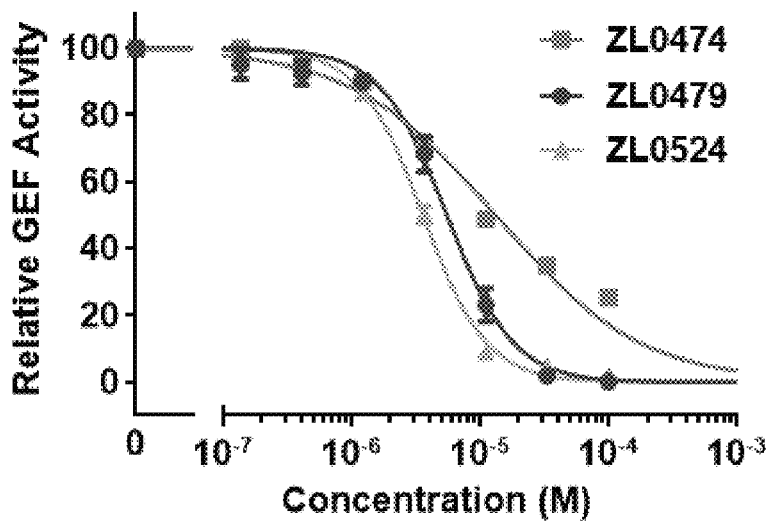
FIG. 7. Relative inhibitory activity for EPAC1-mediated Rap1b-bGDP exchange.
Figure 8:
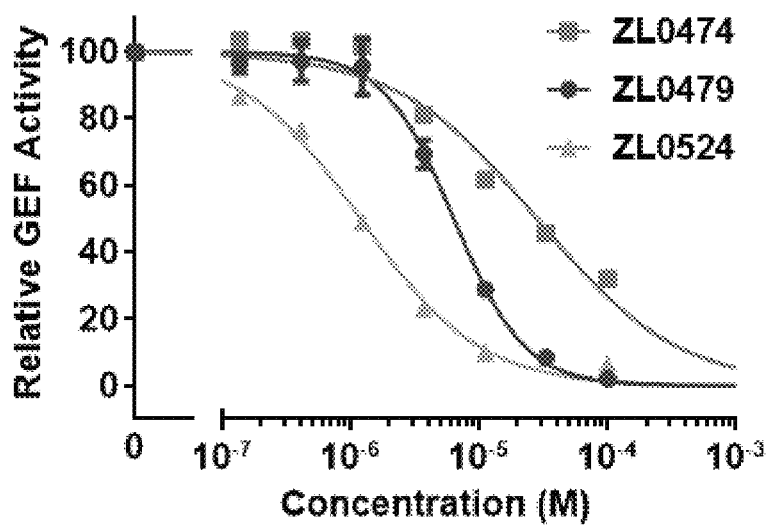
FIG. 8. Relative inhibitory activity for EPAC2-mediated Rap1b-bGDP exchange.

FIG. 7 shows dose-dependent inhibition of EPAC1 GEF activity by compounds 7 (ZL0474), 15 (ZL0479), and 32 (ZL0524), in the presence of 20 μM cAMP. Relative GEF activity were presented as normalized reaction rate constant (means±SEM, n=3) described in the method. FIG. 8 shows dose-dependent inhibition of EPAC$_2$ GEF activity by compounds 7 (ZL0474), 15 (ZL0479), and 32 (ZL0524) in the presence of 20 μM cAMP. Relative GEF activity were presented as normalized reaction rate constant (means±SEM, n=3) described in the method.

The invention claimed is:

1. An Exchange Protein Activated by cAMP (EPAC) antagonist selected from N-(4-Chloro-3-(trifluoromethyl)phenyl)-2-oxo-2-(5-(4-(tert-butyl)phenyl)isoxazol-3-yl)acetohydrazonoyl cyanide (NY0617), N-(3-trifluromethyl-4-chlorophenyl)-2-oxo-2-(5-phenylisoxazol-3-yl)acetohydrazonoyl cyanide (NY0460), N-(3,5-Bis(trifluoromethyl)phenyl)-2-oxo-2-(5-phenylisoxazol-3-yl)acetohydrazonoyl cyanide (NY0457), N-(4-Chloro-3-(trifluoromethyl)phenyl)-2-oxo-2-(5-(4-methoxyphenyl)isoxazol-3-yl)acetohydrazonoyl cyanide (NY0654), N-(3,5-bis(trifluoromethyl)phenyl)-2-(5-(4-methoxyphenyl)isoxazol-3-yl)-2-oxoacetohydrazonoyl cyanide (NY0655), N-(3-Chloro-5-(trifluoromethyl)phenyl)-2-(5-(furan-2-yl)isoxazol-3-yl)-2-oxoacetohydrazonoyl cyanide (NY0725), N-(4-Chloro-3-(trifluoromethyl)phenyl)-2-(5-(furan-2-yl)isoxazol-3-yl)-2-oxoacetohydrazonoyl cyanide (NY0726), or N-(3-Chloro-4-(trifluoromethyl)phenyl)-2-(5-(4-fluorophenyl)isoxazol-3-yl)-2-oxoacetohydrazonoyl cyanide (NY0541).

2. An Exchange Protein Activated by cAMP (EPAC) antagonist having a formula of:

Formula II

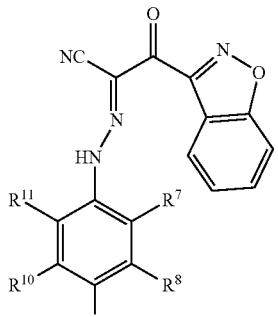

where $R^7$ and $R^{11}$ are H;
$R^8$, $R^9$, and $R^{10}$ are independently selected from H, halogen, CF$_3$, C1 to C4 alkyl, C1 to C4 heteroalkyl, or C1 to C4 alkoxy.

3. The compound of claim 2, wherein $R^8$, $R^9$, $R^{10}$ are independently selected from H, chloro, fluoro, or trifluoromethyl.

4. The compound of claim 2, wherein the compound is selected from 2-(benzo[d]isoxazol-3-yl)-N-(3-chloro-5-(trifluoromethyl)phenyl)-2-oxoacetohydrazonoyl cyanide (NY0495), 2-(benzo[d]isoxazol-3-yl)-N-(3-chloro-4-(trifluoromethyl)phenyl)-2-oxoacetohydrazonoyl cyanide (NY0561), or 2-(benzo[d]isoxazol-3-yl)-N-(4-chloro-3-(trifluoromethyl)phenyl)-2-oxoacetohydrazonoyl cyanide (NY0562).

5. A method of suppressing a microbe infection comprising administering an EPAC specific inhibitor of claim 1 to a subject having or under the risk of a microbe infection.

6. The method of claim 5, wherein the microbe is a bacteria, virus, or fungi.

7. The method of claim 5, wherein the microbe is a bacteria.

8. The method of claim 5, wherein the microbe is a *rickettsia* bacteria.

* * * * *